(12) United States Patent
Padala et al.

(10) Patent No.: US 11,571,305 B2
(45) Date of Patent: Feb. 7, 2023

(54) CARDIAC VALVE LEAFLET ENHANCER DEVICES AND SYSTEMS

(71) Applicant: Emory University, Atlanta, GA (US)

(72) Inventors: Sai Muralidhar Padala, Atlanta, GA (US); Eric Leo Sarin, Atlanta, GA (US)

(73) Assignee: Emory University, Atlanta, GA (US)

(*) Notice: Subject to any disclaimer, the term of this patent is extended or adjusted under 35 U.S.C. 154(b) by 0 days.

(21) Appl. No.: 16/634,107

(22) PCT Filed: Jul. 23, 2018

(86) PCT No.: PCT/US2018/043307
§ 371 (c)(1),
(2) Date: Jan. 24, 2020

(87) PCT Pub. No.: WO2019/023138
PCT Pub. Date: Jan. 31, 2019

(65) Prior Publication Data
US 2020/0205978 A1    Jul. 2, 2020

Related U.S. Application Data

(60) Provisional application No. 62/536,446, filed on Jul. 24, 2017.

(51) Int. Cl.
*A61F 2/24* (2006.01)

(52) U.S. Cl.
CPC ............ *A61F 2/2463* (2013.01); *A61F 2/246* (2013.01); *A61F 2/2466* (2013.01); *A61F 2220/0016* (2013.01); *A61F 2250/0098* (2013.01)

(58) Field of Classification Search
CPC ...... A61F 2/2463; A61F 2/246; A61F 2/2466; A61F 2220/0016; A61F 2250/0098; A61F 2250/0069; A61F 2/24; A61F 2210/0061
See application file for complete search history.

(56) References Cited

U.S. PATENT DOCUMENTS 4,556,060 A    12/1985   Perlin
8,758,431 B2   6/2014    Orlov et al.
(Continued)

FOREIGN PATENT DOCUMENTS

JP    201750673 A    3/2017

OTHER PUBLICATIONS

International Search Report and Written Opinion, issued in connection with International Application No. PCT/US18/43307, dated Oct. 2, 2018.
(Continued)

*Primary Examiner* — Jennifer Dieterle
*Assistant Examiner* — Mihret Tafesse
(74) *Attorney, Agent, or Firm* — Meunier Carlin & Curfman LLC

(57) ABSTRACT

The disclosure relates to a device that is configured to be implanted on the native leaflet of a heart valve to increase its length and/or thickness and thereby to improve the valve function and reduce regurgitation. The device may include a leaflet section. The leaflet section may include a central member. The central member may include a first portion, a second portion that opposes the first portion, and a base portion disposed between the first portion and the second portion. The first section may extend from the first portion and the second section may extend from the second portion. The device may include one or more engaging members extending from the central member at an angle with respect to the first section and the second section. The second section may be larger than the first section. The leaflet section may define a three-dimensional region or a bulge.

20 Claims, 28 Drawing Sheets

(56) References Cited

U.S. PATENT DOCUMENTS

| | | |
|---|---|---|
| 9,011,468 B2 | 4/2015 | Ketai et al. |
| 9,510,948 B2 | 12/2016 | Padala |
| 9,867,704 B2 | 1/2018 | Lee et al. |
| 10,123,873 B1 | 11/2018 | Metchik et al. |
| 10,905,552 B2 | 2/2021 | Dixon et al. |
| 10,925,734 B2 | 2/2021 | Delgado et al. |
| 10,932,908 B2 | 3/2021 | Dixon et al. |
| 11,141,158 B2 | 10/2021 | Ketai et al. |
| 2003/0153946 A1 | 8/2003 | Kimblad |
| 2004/0093023 A1 | 5/2004 | Allen et al. |
| 2004/0220593 A1* | 11/2004 | Greenhalgh .......... A61F 2/2454 606/151 |
| 2005/0216039 A1 | 9/2005 | Lederman |
| 2006/0293698 A1 | 12/2006 | Douk |
| 2007/0197858 A1 | 8/2007 | Goldfarb et al. |
| 2008/0051807 A1 | 2/2008 | St. Goar et al. |
| 2014/0067048 A1 | 3/2014 | Chau et al. |
| 2015/0230919 A1 | 8/2015 | Chau et al. |
| 2016/0287387 A1 | 10/2016 | Wei |
| 2016/0317290 A1 | 11/2016 | Chau et al. |
| 2017/0020521 A1 | 1/2017 | Krone et al. |
| 2018/0147054 A1 | 5/2018 | Chau et al. |
| 2018/0185154 A1 | 7/2018 | Cao |

OTHER PUBLICATIONS

Search Report, issued in EP Application No. 18837757.6 (PCT/US2018043307), dated Mar. 31, 2021.

Padala, Sai Muralidhar, and Eric Leo Sarin. (Oct. 16, 2016). MitraPlug: Transcatheter leaflet extending for mitral & tricuspid repair [PowerPoint presentation], TCT Conference, Cardiovascular Research Foundation, Washington D.C.

English translation of Japanese Office Action issued in JP 2020-503766, dated Jul. 29, 2022.

* cited by examiner

500

500

700

710

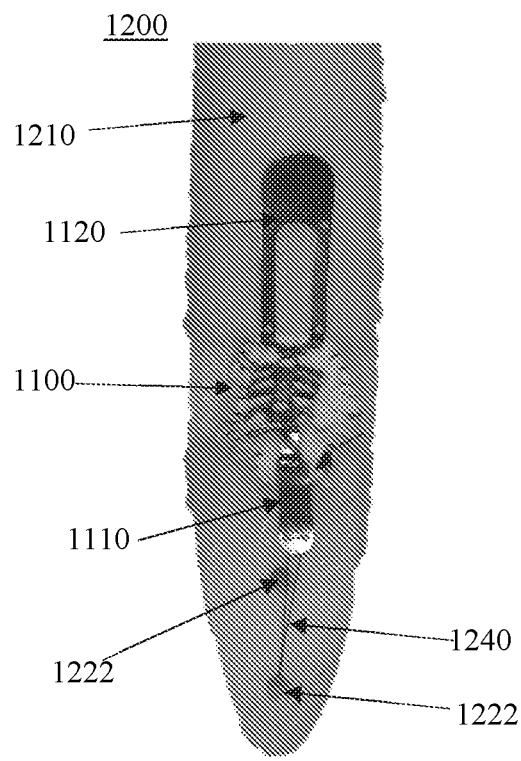
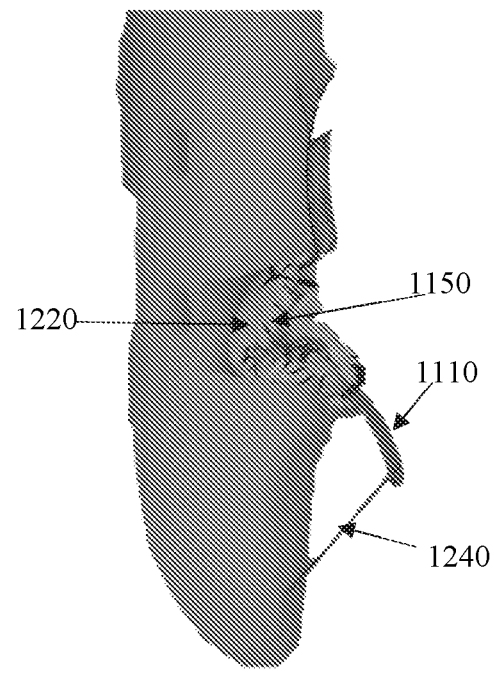
FIG. 12A          FIG. 12B
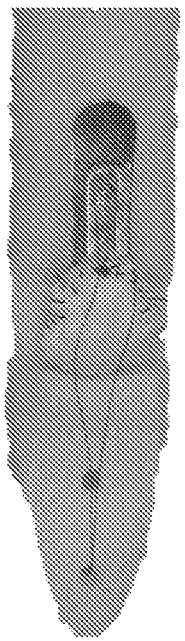
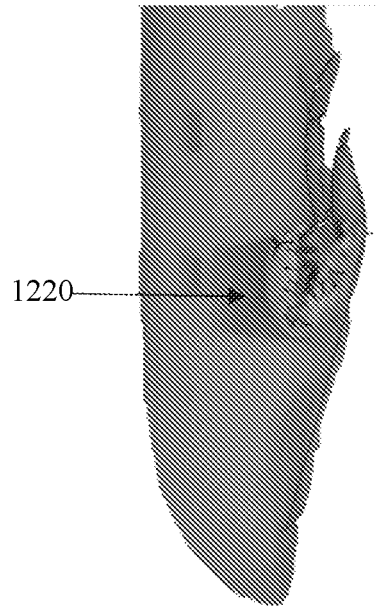
FIG. 12C          FIG. 12D

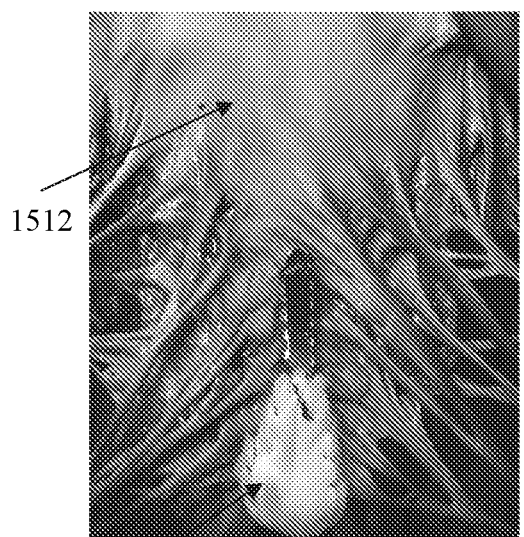
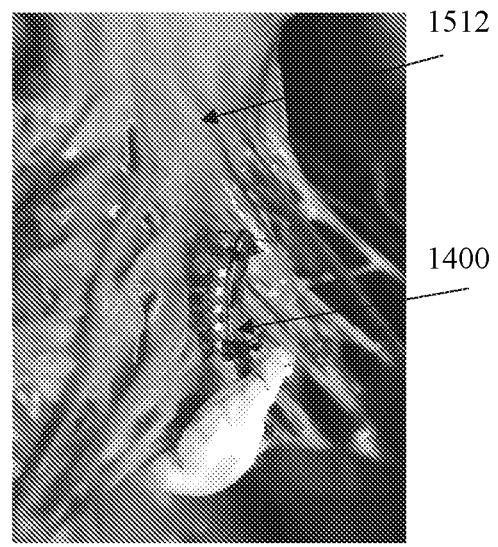
FIG. 15A
FIG. 15B
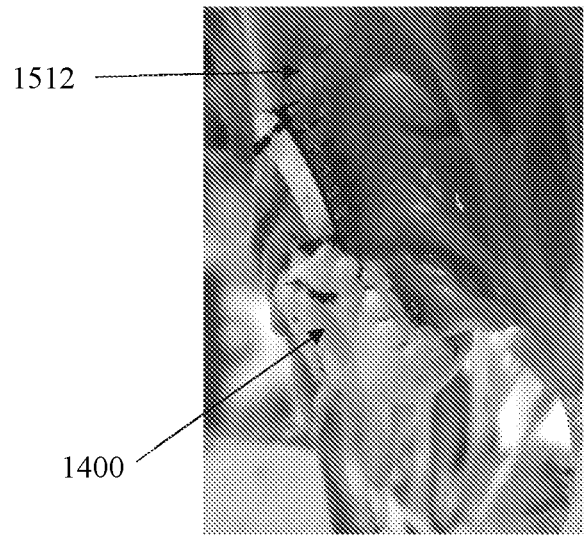
FIG. 15C

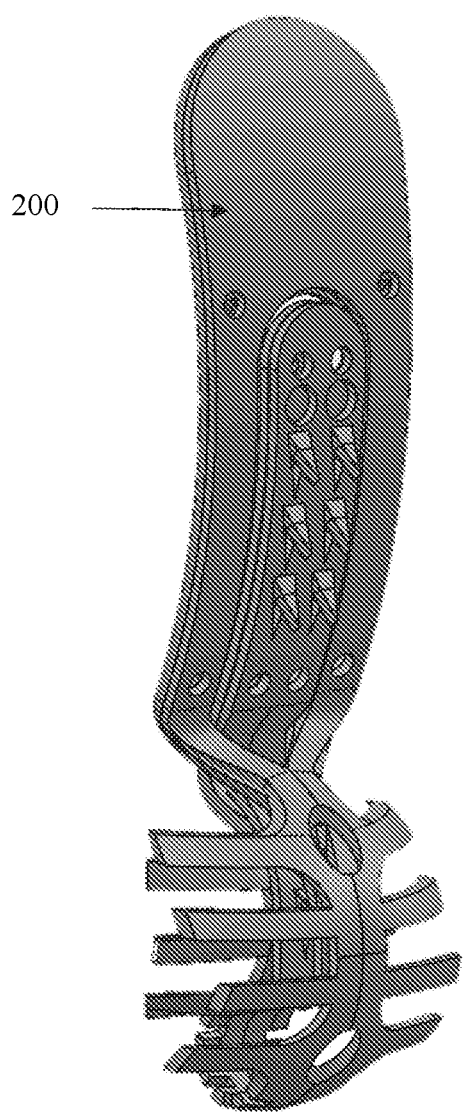
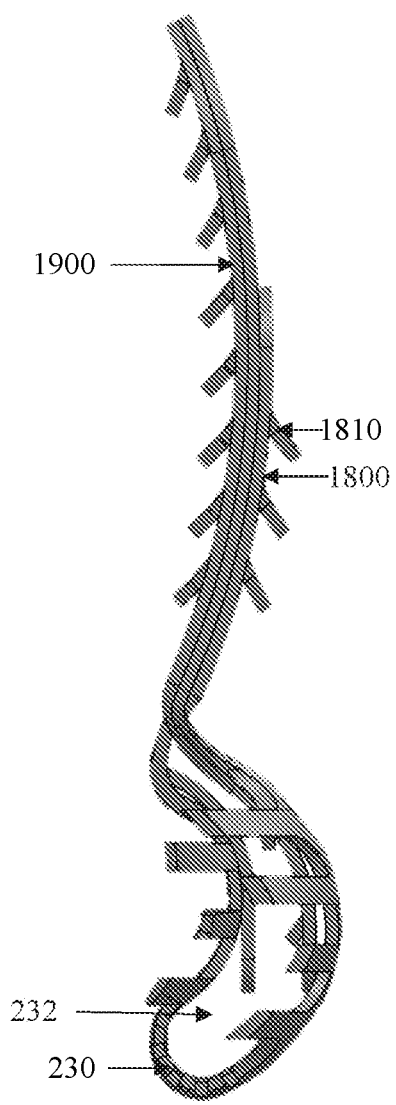
FIG. 16A
FIG. 16B

CARDIAC VALVE LEAFLET ENHANCER DEVICES AND SYSTEMS

CROSS-REFERENCE TO RELATED APPLICATIONS

This application is the National Stage of International Application No. PCT/US2018/043307 filed Jul. 23, 2018, which claims the benefit of U.S. Provisional Application No. 62/536,446 filed Jul. 24, 2017. The entirety of each of these applications is hereby incorporated by reference for all purposes.

STATEMENT REGARDING FEDERALLY SPONSORED RESEARCH OR DEVELOPMENT

This invention was made with government support under HL135145 awarded by the National Institutes of Health. The government has certain rights in the invention.

BACKGROUND

Cardiac valves play a critical role in maintaining unidirectional blood flow through the heart in each cardiac cycle. The atrioventricular valves (i.e. the mitral and tricuspid valves) located between the atria and the ventricles regulate unidirectional blood flow returning either from the pulmonary or venous systems into the heart, and the semilunar valves (i.e. the aortic and pulmonary valves) maintain unidirectional blood flow between the ventricle and the aorta and pulmonary arteries. Regurgitation or backflow of blood through any of these valves can lead to congestive heart failure and death, and therefore restoration of valve competence through repair or replacement is necessary.

The atrioventricular valves regurgitate more frequently than the semilunar valves. The mitral valve when functioning properly ensures unidirectional blood flow from the left atrium into the left ventricle. The mitral valve has two leaflets, the anterior leaflet and the posterior leaflet, which are connected to a cartilaginous annular ring on one end and to the papillary muscles on the other end, via the chordae tendineae. In systole, higher left ventricular pressure and lower left atrial pressure enables basal motion of the anterior and posterior mitral leaflets towards the annulus and each other, facilitating tight closure of the valve and no backflow of blood. In diastole, lower left ventricular pressure and higher left atrial pressure ensure retraction of the leaflets away from one another and the opening of the mitral orifice to allow left ventricular filling.

In some diseases of the mitral valve, rupture of the chordae tendineae with or without expansion of the valve leaflets can cause improper closure of the valve leaflets and thus regurgitation. In other diseases of the left ventricle, injury, dilatation, and dyskinesia of the ventricular myocardium from cardiomyopathies can perturb the native mitral valve geometry and restrict the leaflets from proper closure leading to regurgitation. In either case, regurgitation can occur through a small gap between the two leaflets, because the leaflets override each other or because they are retracted away from each other from annular and/or ventricular tethering.

Similarly, the tricuspid valve maintains unidirectional blood flow through the right atrium into the right ventricle. Under similar circumstances as the mitral valve, regurgitation can also occur either due to primary lesions of the valve such as chordal rupture or leaflet prolapse, or from secondary right ventricular dilatation. Tricuspid regurgitation can also be common among patients with a pacemaker, as the lead from the pacemaker passes through the tricuspid valve and can impair leaflet closure, leaving a gap.

In all cases, valve regurgitation can impair efficient function of the heart and thus requires repair in a timely and appropriate manner to restore valve competence.

SUMMARY

Thus, there is a need for devices and/or methods that can correct regurgitation and restore efficient cardiac function.

For example, the devices and methods according to embodiments can correct regurgitation by altering the physical dimensions, features and properties of a cardiac valve leaflet to thereby change the configuration of the valve leaflet so that it overlaps with another leaflet of the same valve and ensures proper closure of the valve and correction of regurgitation.

In some embodiments, the devices may include a device. The device may include a leaflet section. The leaflet section may include a central member. The central member may include a first portion, a second portion that opposes the first portion, and a base portion (or third portion) disposed between the first portion and the second portion. The device may include a first section that extends from the first portion and a second section that extends from the second portion. In some embodiments, the device may further include one or more engaging members extending from the central member and extending perpendicular to the first section and the second section.

In some embodiments, the leaflet section may define a three-dimensional region or a bulge. In some embodiments, the leaflet section, the first portion and the second portion may be part of the device body.

In some embodiments, the second section may be larger than the first section. In some embodiments, the second section may include an opening.

In some embodiments, the device may be configured to move between a closed configuration and an open configuration. The closed configuration may be the default configuration. In the closed configuration, the first section may be configured to be disposed within the opening of the second section. In some embodiments, in the closed configuration, the first section may be biased towards the second section so that the first section and second section are coplanar.

In the open configuration, the first section may be disposed away from the second section.

In some embodiments, the one or more engaging members may include a first set of engaging members extending from the first portion and a second set of engaging members extending from the second portion. The first set of engaging members may include less engaging members than the second set of engaging members. In some embodiments, each of the first set of engaging members and the second set of engaging members may include a plurality of rows of engaging members.

In some embodiments, each engaging member may extend at an angle from the central member. In some embodiments, the angle at which each engaging member extends may be between about 30 degrees and 150 degrees. In some embodiments, one or more engaging members may be perpendicular to the central member.

In some embodiments, the device may further include at least one covering member. The covering member may be disposed on the leaflet section. In some embodiments, the covering member may extend past the leaflet section in one or more directions.

In some embodiments, the covering member may include a first end, a second end, and a length there between. The covering member may include a spine that extends from the first end and the second end. In some embodiments, the spine may include a flexible member. In some embodiments, the flexible member may be tapered.

In some embodiments, the spine configured to attach to at least a part of the central member of the leaflet section. In some embodiments, the spine may be configured to attach to the entire central member. In some embodiments, the spine may be configured to attach to the first and/or section.

In some embodiments, the first and second sections may be configured to compress upon opposite surfaces of the native leaflet when implanted.

In some embodiments, each of the first portion and the second portion may include a curvature so that the leaflet section protrudes towards the second section. In some embodiments, the first portion may protrude in a direction toward the second portion. The second portion may protrude outwardly in the direction.

In some embodiments, the device may also include one or more gripping members extending from a surface of the first section and/or the second section. In some embodiments, the one or more gripping members may include but are not limited to protrusions, such as teeth. In some embodiments, the one or more gripping members may be configured to puncture partially or completely the native leaflet when the device is implanted.

In some embodiments, the device may also include one or more plates configured to be attached to the first section and/or the second section. The one or more plates may include the one or more gripping members configured to contact the native leaflet. The one or more gripping members may protrude from the one or more plates towards the leaflet section. In some embodiments, the one or more plates may be configured to extend within the leaflet section.

In some embodiments, the one or more plates may include a first plate configured to attach to the first section and a second plate configured to attach to the second section. In some embodiments, the first plate and the second plate may be connected to another plate so at form an integral plate body.

In some embodiments, the devices may include a device. In some embodiments, the device may include a leaflet section. The device may include a first section extending from the leaflet section and a second section extending from the leaflet section. The second section may include an opening and may be larger than the first section.

In some embodiments, the device may be configured to move between a default, closed configuration and an open configuration. The device may biased to the closed configuration. In the closed configuration, the first section may be biased towards the second section so that the first section and the second section are coplanar and that the first section may be disposed within the opening. In the closed configuration, the first section and the second section may be configured to impose a compressive force on opposite surfaces of a native leaflet captured there between.

In some embodiments, the leaflet section may define a three-dimensional region or bulge. The leaflet section may include a central member. In some embodiments, the central member may include a first portion, a second portion that opposes the first portion, and a base portion disposed between the first portion and the second portion. The first section may extend from the first portion; and the second section may extend from the second portion.

In some embodiments, the first section and second section may be parallel to each other and include a space separating the first section and the second section. In some embodiments, the first section and the second section may be aligned with each other.

In some embodiments the device may further include one or more engaging members extending from the central member. In some embodiments, each engaging member may extend at an angle from the central member. In some embodiments, the angle at which each engaging member extends may be between about 30 degrees and 150 degrees. In some embodiments, one or more engaging members may be perpendicular to the central member.

In some embodiments, the devices may be machined from a single sheet of material. The material may include but is not limited to a shape memory alloy, such as Nitinol.

In some embodiments, the one or more engaging members may include a first set of engaging members extending from the first portion and a second set of engaging members extending from the second portion. The first set of engaging members may be different from the second set of engaging members. Each of the first set of engaging members and the second set of engaging members may include a plurality of rows of engaging members.

In some embodiments, the first set of engaging members may include less engaging members than the second set of engaging members. In some embodiments, the first set of engaging members and the second set of engaging members may differ in length and/or curvature.

In some embodiments, the device may also include a covering member. The covering member may be disposed on and surround at least the leaflet section. In some embodiments, the covering member may extend beyond the leaflet section in one or more directions.

In some embodiments, the covering member may include a first end, a second end, and a length there between. The covering member may include a spine that extends from the first end and the second end. In some embodiments, the spine may include a flexible member. In some embodiments, the flexible member may be tapered.

In some embodiments, the spine configured to attach to at least a part of the central member of the leaflet section. In some embodiments, the spine may be configured to attach to the entire central member. In some embodiments, the spine may be configured to attach to the first and/or section.

In some embodiments, the first portion and the second portion may a curved profile in the closed configuration. In some embodiments, the first portion may protrude towards the second portion in the closed configuration. The leaflet section may be configured to surround an edge of the native leaflet and extend along opposing surfaces of the native leaflet when the device is implanted.

In some embodiments, the device may include one or more gripping members extending from a surface of the first section and/or the second section. In some embodiments, the one or more gripping members may include but are not limited to protrusions, such as teeth. In some embodiments, the one or more gripping members may be configured to puncture partially or completely the native leaflet when the device is implanted.

In some embodiments, the devices may include one or more plates disposed on the first section and/or second section. Each plate may be configured to be attached to the first section and/or the second section. The one or more plates may include one or more gripping members extending from a surface of the first section and/or the second section.

In some embodiments, the one or more gripping members may protrude from the plates towards the leaflet section. In some embodiments, the one or more plates may be configured to extend within the leaflet section.

In some embodiments, the one or more plates may include a first plate configured to attach to the first section and a second plate configured to attach to the second section. In some embodiments, the first plate and the second plate may be connected to another plate so at form an integral plate body.

In some embodiments, the device may be configured to be delivered using a delivery catheter. The delivery catheter may be configured to deliver the device in the open configuration to the native leaflet and move the device to the closed configuration for attachment to the native leaflet.

In some embodiments, the systems may include a system that includes the leaflet enhancer device and the delivery catheter.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

FIGS. 12A-D show views of the prototype shown in FIGS. 11A-C disposed in a delivery device according to some embodiments;

FIGS. 15A-C show the prototype shown in FIGS. 14A-D implanted on a native leaflet and pictured from the ventricular side of the leaflet;

FIGS. 16A and B show views of a leaflet enhancer device according to some embodiments;

DETAILED DESCRIPTION OF THE EMBODIMENTS

Figure 1A:
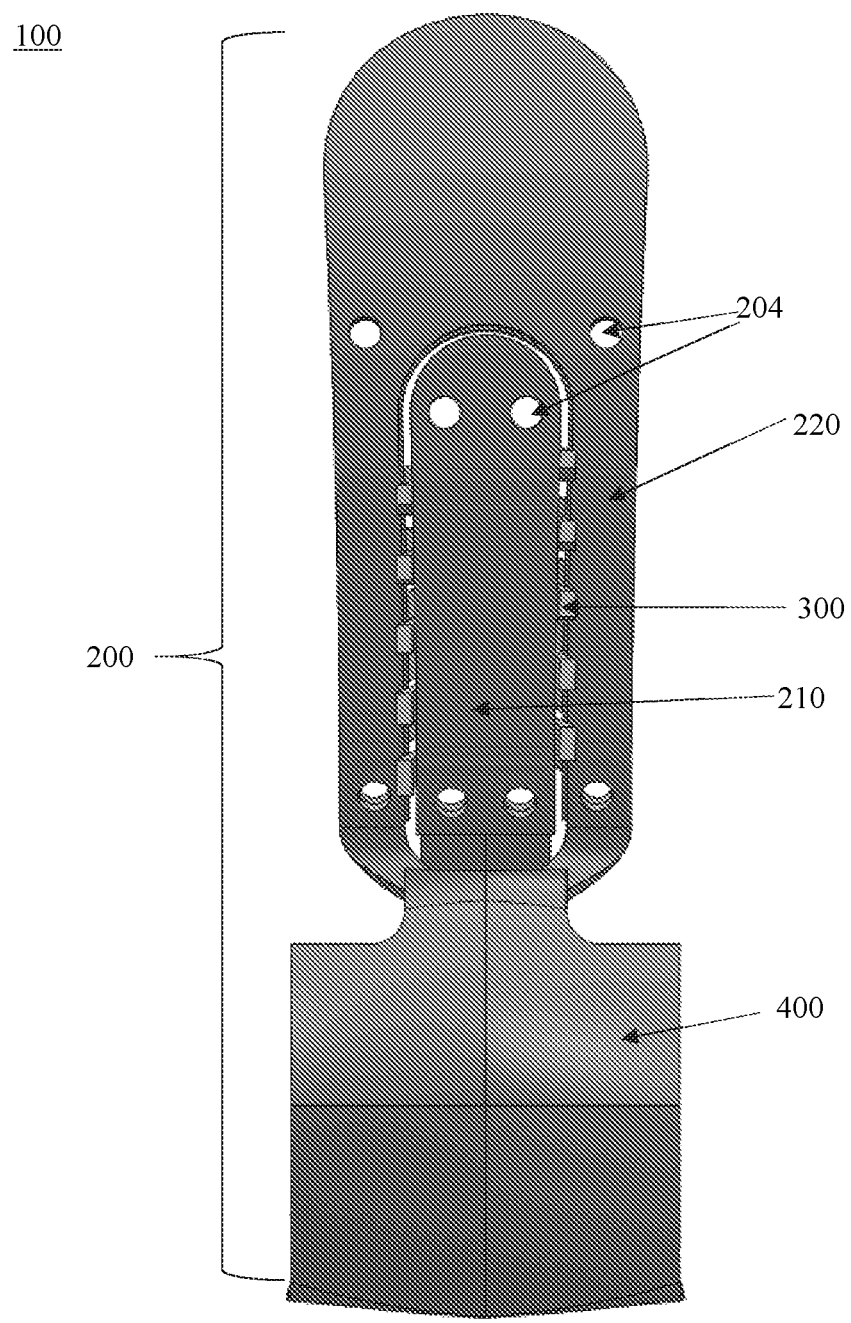
FIGS. 1A and 1B show views of a leaflet enhancer device according to some embodiments.

This disclosure pertains generally to prosthetic implantable devices and systems to reduce or eliminate heart valve regurgitation by modifying the physical and/or functional properties of the native leaflet, and related methods for implantation of such devices in the heart. In the following description, numerous specific details are set forth, such as examples of specific components, devices, methods etc., in order to provide a thorough understanding of embodiments of the disclosure. It will be apparent, however, to one skilled in the art that these specific details need not be employed to practice embodiments of the disclosure. In other instances, well known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The disclosed devices, methods and systems can include one or more sections that can enhance or alter the physical and kinematic characteristics and properties of a cardiac valve leaflet and thereby can improve valve closure and eliminate leakage. The physical characteristics may include but are not limited to leaflet length, leaflet thickness, leaflet curvature, leaflet shape, leaflet height, leaflet mobility, etc., and/or any combination. Other properties may include but are not limited to (i) leaflet stiffness, leaflet strain and/or stress under transvalvular pressure, (ii) leaflet shape in the systolic and/or diastolic phases of the cardiac cycle, and/or (iii) any combination thereof. These properties may be altered at a specific regions of the leaflet, or the entire leaflet. When implanted, the devices and systems may treat regurgitation of blood through a valve by enhancing or altering any or all of the above characteristics and properties.

In some embodiments, the disclosed (leaflet enhancer) devices may have a 3-dimensional shape such that the device can be configured to be disposed on some part of the leaflet of a desired native valve. The region of the native valve onto which the device is disposed on may be determined by the physician prior to the device deployment, under direct visual assessment of the valve or via non-invasive imaging techniques such as MRI, CT, Ultrasound, Fluoroscopy etc., but not limited to these modalities. The devices may be configured such that upon being disposed on the leaflet of a native valve, they may alter the physical characteristics and properties of the region of the native valve leaflet onto which the device is disposed, and/or may alter the same of the entire native valve leaflet onto which the device is disposed. Changes in these physical characteristics and properties of the native valve may result in changes in the motion, deformation and/or stretch of the native valve leaflet onto which the device is disposed.

In some embodiments, the disclosed devices may include a first section or arm (also referred to as ventricular arm or section), a second section or arm (also referred to as atrial arm or section), and a leaflet section. In some embodiments, the first section and the second section may be connected to each other by the leaflet section. In some embodiments, the first and second sections may be configured to be positionable on respective sides of a native leaflet and the leaflet section may be configured to protrude from the end of the native leaflet so as to change the physical characteristics and/or properties of that leaflet. In some embodiments, the first and second sections may be configured to have a linear or coplanar profile in a closed or default configuration.

In some embodiments, leaflet section may be configured to have a three-dimensional profile. In some embodiments, the leaflet section may include a three-dimensional region. In some embodiments, the leaflet section may have a substantially curved profile. In some embodiments, the leaflet section may have a different profile, such as a flat profile. In some embodiments, the profile and/or shape of the sections may be determined based on the desired anatomical location on the native leaflet on which the device is configured to be implanted.

In some embodiments, the disclosed devices (e.g., the ventricular, atrial and/or leaflet sections) may be configured such that the type or extent of physical characteristic or property of the native leaflet to be enhanced or altered can be selected on a patient specific basis. For example, if the thickness of the native leaflet at a specific region needs to be enhanced in a patient, the leaflet section can achieve this enhancement without altering the leaflet height. In another example, the height of the leaflet can be altered by the ventricular and/or atrial sections when implanted without altering the thickness, etc., and such combinations may be numerous and not limited to those described here.

In some embodiments, the first and second sections may have a similar or different shape and/or size. In some embodiments, the first and second sections may have a similar shape and a different size. By way of example, the first section and the second section may have an elongated circular, tapered shape. In some embodiments, both the first and the second sections may taper (e.g., widen) along the length from the leaflet section toward an end. In some embodiments, one or more of the first and second sections may include a central opening. For example, the second (atrial) section may have an opening that is larger than the first (ventricular) section so that the smaller, first (ventricular) section can be positioned in the plane of the second (atrial) section, within the opening in the second (atrial section). The smaller first (ventricular) section can also reduce the risk of that section touching the myocardium underlying the native leaflet, during deployment (e.g., opening of the first and second sections to receive the native leaflet). By having at least smaller first section, the leaflet device may also be opened to a larger angle without interfering with the myocardium. In some embodiments, the second section may be smaller than and/or substantially the same size as the first section.

In some embodiments, the devices may be configured to move between a first configuration and a second configuration. In the first or default configuration, the device may be in a closed configuration in which the first and second sections are substantially aligned in a curved, planar profile. The first and second sections may be biased toward the closed configuration. The leaflet section may a three-dimensional profile from which the first and second sections extend. In the second or open configuration, the first and second sections may be disposed to extend from opposite sides of the leaflet section away from each other with an angle between the two sections. The devices may move between the first configuration to the second configuration by causing the first section and/or the second section to bend or move away from each other and thereby forcing the device into an open configuration. By opening the device by moving the first section and the second section away from each other and/or the leaflet section, the leaflet section may also be caused to temporarily change shape. When the first and second sections are allowed to revert to the closed position, the leaflet section may also revert to the default position.

By configuring the first and second sections to be biased towards a coplanar alignment, the first section and the second section may cause the leaflet to be captured and compressed between the first section and second section when the devices are implanted on a leaflet so that a first section is disposed on the ventricular side of the leaflet and the second section is disposed on the atrial side of the leaflet. When the device is placed in the open configuration so that the device can be mounted on the native leaflet, the biasing force applied by the first section and the second section causes the first section and the second section to bear against the tissue on respective sides of the native leaflet and clamp or compress the native leaflet there between. This can result in the device be fixedly attached to the native leaflet. In some embodiments, the biasing force of the first section and the second section can be sufficient to retain the device on the native leaflet without an additional securing mechanism extending through the leaflet (e.g., such as a suture). In this example, the leaflet section may be disposed to surround the end of the native leaflet and at least a part of the opposing surfaces of the native leaflet.

In the default configuration where the first section and the second section are close to each other, the first and second sections may be positioned such that the space or distance between them may be smaller than the thickness of the native leaflet. In some embodiments, in the closed or default configuration, the first section and the second section may be parallel with respect to a planar profile or axis. In some embodiments, in the closed or default configuration, there may be substantially no distance between the first section and the second section so that the first section and the second section are substantially aligned with the planar profile or axis of the device. In some embodiments, in the closed or default configuration, there may be a distance between the first section and the second section that is smaller than the thickness of the native leaflet. In some embodiments, the first section and/or the second section may include one or more tissue gripping members disposed on a surface facing the native leaflet and configured to engage the respective tissue. In some embodiments, the one or more tissue gripping members may include but are not limited to protruding members (e.g., teeth, barbs, among others, or a combination thereof), textured surface, grooves, among others, or a combination thereof. For example, the one or more tissue gripping members may be cut into the first and/or second sections and bent at an angle so that they are perpendicular or at an angle in relation to the respective section resulting in protrusions from that respective section. In another example, the tissue gripping members may be disposed on one more plates, and then attached to the respective first or second sections. The one or more tissue gripping members may be configured to enhance the attachment of the respective first and/or second sections to the native leaflet by increasing the friction between these sections and the native leaflet captured there between.

In some embodiments, the one or more tissue gripping members may be configured interact with and/or deform the native tissue. In some embodiments, the one or more tissue gripping members can increase friction by partially or fully piercing into the native leaflet and thus provide increased friction. In some embodiments, one or more gripping members may be disposed the first and second sections of the device body in alternating pattern so as to no directly oppose each other. This way, the alternating gripping members disposed on either side of the leaflet may increase friction. In some configurations, the one or more gripping members may differ between the first and second sections, along the first and section sections, among others, or a combination thereof. In some configurations, the gripping members may only cover partially or entirely cover the section to which they are attached and/or from which they are protruding.

In some embodiments, the leaflet section may protrude from the first and second sections so as to have a three-dimensional profile or shape with respect to the first and second sections. In this way, the leaflet section may define a bulge (the three-dimensional shape or profile) when implanted onto a native leaflet. In some embodiments, the leaflet section may include a first portion, which is an extension of the first section, and a second portion, which is an extension of the second section. Each portion may protrude in a direction to define the bulge. When implanted on a native leaflet, the bulge associated with the second portion may protrude from the surface of the native leaflet that it is disposed on, while the bulge associated with the first portion may protrude into the native leaflet towards the bulge of the second portion, thereby increasing the force of device attachment to the native leaflet.

In some embodiments, the leaflet section may have a different profile with respect to the first and second sections. In some embodiments, the leaflet section may have a less curved profile. In some embodiments, the leaflet section may have a substantially flat profile with respect to the first and second sections.

The leaflet section of the device may configured to distribute stresses associated with the valve functions. In some embodiments, the leaflet section may be configured to change the physical characteristics of the native leaflet, including but not limited to, increase thickness, length and/or height of the native leaflet when the device implanted on the native leaflet. For example, the leaflet section may have dimensions (e.g., bulging height relative to the first/second sections/portions, length, width, etc.) that can be configured to alter the characteristics and/or properties of the native valve leaflet. By changing the physical properties of the native leaflet to which the device is mounted, the device may also alter the mechanics and/or function of the opposing leaflet that interacts with the native leaflet.

In some embodiments, the devices may include one or more covering members configured to at least cover the leaflet section. In some embodiments, the one or more covering members may also cover at least a part of the first section and/or second section. The one or more covering members can be configured to increase the curvature, thickness and/or other dimensions of the leaflet section on which the one or more covering members is attached, and enable better adhesion of the device when implanted. The covering member(s) can also provide a softer surface for the opposite leaflet to interact with, and thereby can reduce the potential risk of damage to the leaflet opposite to the one with the implant. The covering member(s) may also extend beyond the leaflet section in the orthogonal direction, such that the leaflet section with the covering member(s) may be longer in a direction than the leaflet section (alone). In some embodiments, the covering member(s) may be configured to be attached at its two ends to a part of the first or second section of the device, or may be configured to be attached at different points between the first and the second sections. In some embodiments, the covering member(s) may be flexible, so that the device assembly may be inserted into a catheter of small dimensions, by compressing the flexible covering member.

In some embodiments, the one or more covering members may be made of one or more materials, layers, or a combination thereof. The one or more covering members may include one or more shape memory materials. The one or more covering members may be configured to be temporarily compressed when inserted into a delivery device and be configured to return to the default shape when the leaflet device including the covering member(s) is delivered from the delivery device.

In some embodiments, the one or more covering members may be disposed partially and/or entirely along the central member of the leaflet section and/or the first section and/or the second sections. In some embodiments, the one or more covering members may have a width that is larger than the width of the leaflet device. This way, the covering member may extend beyond the device horizontally when disposed on the leaflet device. In some embodiments, the one or more covering members may have a shape that changes along the width and/or length. For example, the one or more covering members may taper from a center of the one more covering member towards the ends.

In some embodiments, the devices may be delivered via a delivery device in a fully or partially open configuration. The devices may be in a fully or partially open configuration. In some embodiments, each section may include one or more coupling members configured to engage a corresponding coupling member of one or more accessories (e.g., attachment plates with tissue gripping members, covering members, among others, or a combination thereof) and/or of a delivery device configured to position the device in an open or expanded configuration. In some embodiments, the one or more coupling members may be configured to fasten to complementary coupling members disposed on the delivery device. For example, the one or more coupling members may include but are not limited to one or more openings, grooves, protrusions, depressions, among others, or a combination thereof. In some embodiments, the one or more coupling members may be configured to removably or fixedly fasten to the complementary coupling members using one or more fastening members, such as wires, sutures, flexible tubes, among others, or a combination thereof. The sections may include the same and/or different one or more coupling members. For example, the coupling members may be the same and/or different with respect to shape, size, type, number, among others, or a combination thereof.

FIGS. 1-6B and 8A-21B show examples of leaflet enhancer devices according to some embodiments. It will be understood that the leaflet enhancer devices are not limited to the configuration and/or combination of the first sections, second sections, leaflet sections, engaging members, coupling members, gripping members, plates, and/or the covering members as shown and described with respect to the figures. The leaflet enhancer devices may include any combination of the embodiments of the first sections, second sections, and the leaflet sections.

Figure 1B:
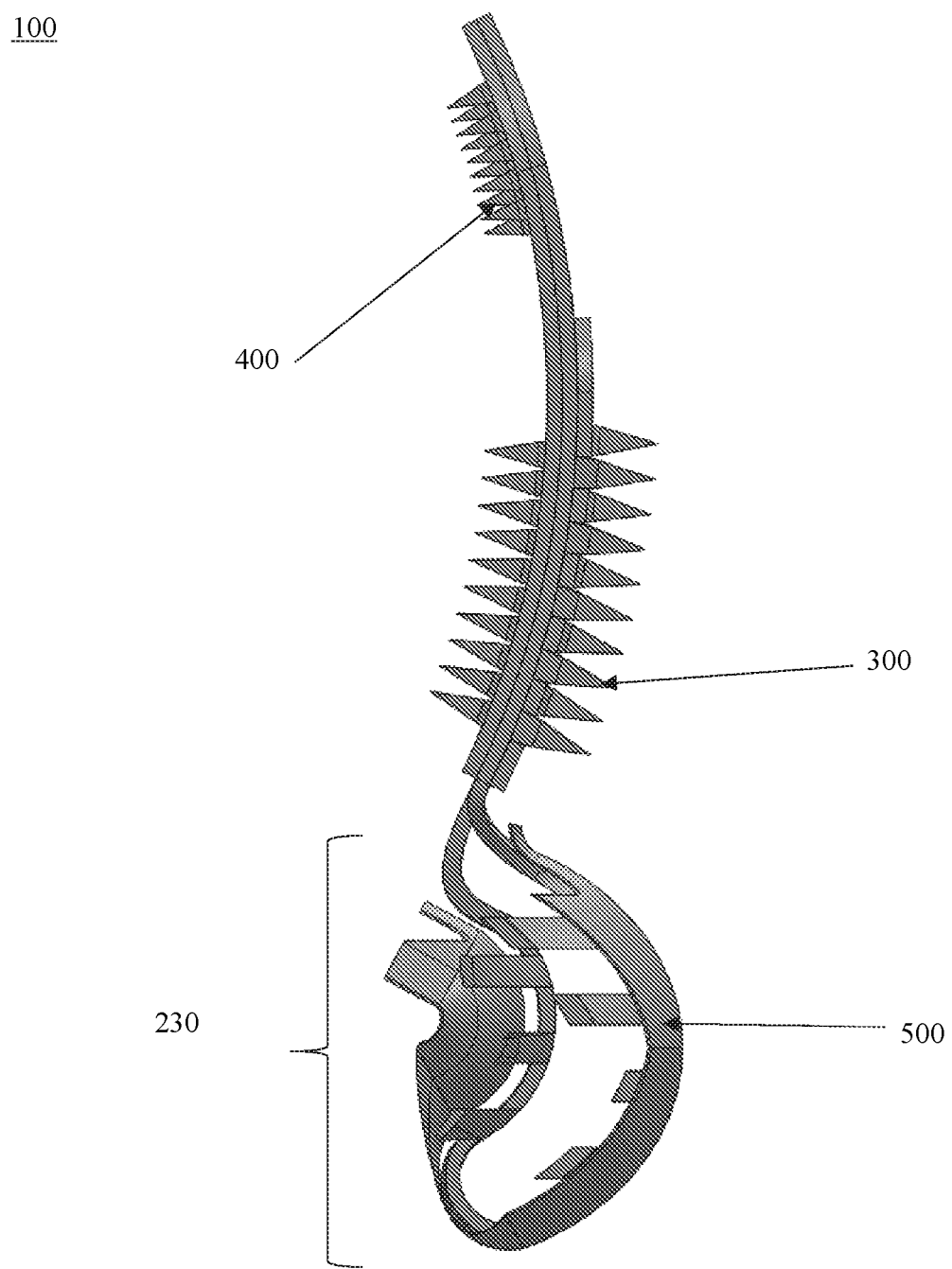

FIGS. 1A and 1B show views of a leaflet enhancer device 100 according to some embodiments. In some embodiments, the device 100 may include a first (ventricular) section or arm 210, a second (atrial) section or arm 220, and a leaflet section 230. In some embodiments, each of the first section 210 and the second section 220 may be connected to the leaflet section 230 and may be configured to extend from the leaflet section 230. The first section 210, the second section 220 and the leaflet section 230 may be referred to as device body 200.

In some embodiments, the device 100 may include one or more gripping members disposed on the first and/or second sections. As shown in FIGS. 1A and 1B, the device 100 may include a plurality of gripping members 300 disposed on (e.g., protruding from) a surface 211 of the first section 210 that is configured to face a surface of a native leaflet and a plurality of members 400 disposed on (e.g., protruding from) a surface 221 of the second section 220 that is configured to face the opposing surface of the native leaflet.

In some embodiments, the device 100 may include one or more covering members 500. In some embodiments, the device 100 may include one or more covering members 500 disposed on the leaflet section 230 and/or configured to surround or wrap the leaflet section 230. In some embodiments, the one or more covering members 500 may be configured to partially cover the first section 210 and/or the second section 220. The covering member(s) 500 may be specific to the geometry of the valve defects of the patient and may enable better adhesion of the device when implanted and better covering of the regurgitant orifice.

FIGS. 2A-5B show enlarged, unobstructed views of the components of the device 100. FIGS. 2A-2F show different views of the device body 200 (the first section 210, the second section 220, and the leaflet section 230) shown in FIGS. 1A and B isolated from the gripping members 300 and 400, and the covering member 500. FIGS. 2A-2E show the device body 200 in the closed configuration, which can correspond to the first or default configuration.

In some embodiments, the leaflet section 230 may include a central member 240 (also referred to as a hinge or spine) having a first end 241, a second end 243 and a length therebetween. In some embodiments, the central member 240 may include a first portion 250, a second portion 260, and a base portion 270 disposed between the first portion 250 and the second portion 260. The first portion 250 may have a length 251 that extends between the first end 241 and the base portion 270; and the second portion 260 may have a length 261 that extends between the second end 243 and the base portion 270. In some embodiments, the first portion 250 may be disposed on the ventricular side of the native leaflet and the second portion 260 may be disposed on the atrial side of the native leaflet.

In the first or default configuration, the first portion 250 may oppose the second portion 260 to define a leaflet region 232 in which at least a part of the native leaflet may be inserted so as to be surrounded by the leaflet section 230 when the device 100 is mounted onto a native leaflet. The base portion 270 may be disposed at the bottom of the leaflet region 230 and may be considered the lowest point or bottom of the device body 200. In some embodiments, the base portion 270 may include one or more grooves 272 disposed along the length, as shown in FIG. 2F. The one or more tissue engaging members may extend from the central member 240. The one or more grooves 272 may be offset. The one or more grooves 272 can provide flexibility and reduce stress concentration at the base portion because the body 200 is folded or bent about the base portion 270 to form a curve.

In some embodiments, the length 251 of the first portion 250 may be shorter than the length 261 of the second portion 260, as shown in FIGS. 2A-2F. In some embodiments, the length 251 of the first portion 250 and the length 261 of the second portion 260 may be the same or different.

In some embodiments, the leaflet section 230 may have a three-dimensional shape. In some embodiments, the first portion 250 and/or the second portion 260 may have a curved shape or profile (also referred to as the bulge or three-dimensional shape). For example, in some embodiments, the first portion 250 and/or the second portion 260 may be disposed so that the leaflet section 230 protrudes relative to at least the second section 220 in a direction to define a three-dimensional shape or a bulge. By way of example, the first portion 250 and the second portion 260 may be configured to protrude towards a direction relative to the planar profile P, for example, to define a convex curvature, for example, as shown in FIG. 2E. The first portion 250 and the second portion 260 may curve outwards to the same direction relative to the planar profile P of the first section 210 and the second section 220. By way of example, the first portion 250 may include a curvature towards or include a bulge that protrudes in the direction towards the second portion 260, and the second portion 260 may include a curvature towards or include a bulge that protrudes outwardly in the same direction. In this example, the curvature of the first portion 250 may be disposed within the curvature of the second portion 260.

In some embodiments, the first portion 250 and the second portion 260 may have the same amount of curvature or a different amount of curvature. For example, the curvature of the first portion 250 may be proportional to the curvature of the second portion 260. In some embodiments, the amount of curvature may relate to the length of these portions. In some embodiments, the second portion 260, which has a longer length than the first portion 250, may have a radius of curvature that is larger than a radius of curvature of the first portion 250, as shown in FIG. 2D. In this example, the curved profile or curvature of section 250 of the leaflet section 230 can enable better attachment of the device to a native (e.g., mitral) valve leaflet on the ventricular side.

It will be understood that the first portion 250 and the second portion 260 may have a different amount of curvature. For example, the amount of curvature of one or both portions 250 and 260 can be determined such that it conforms to the systolic curvature of the leaflet in systolic phase of a heartbeat of a patient in which the device may be implanted.

In some embodiments, the device 100 may include one or more sets of one or more engaging members 280 extending from the central member 240 in one and/or two directions (e.g., opposing directions). In some embodiments, the one or more engaging members 280 may be disposed so as to extend at an angle in one or both sides of the central member 240 along at least the leaflet section 230. In this example, the one or more engaging members 280 may be configured to define the leaflet region 232.

In some embodiments, the angle at which each engaging member may extend from the central member 240 may between about 30 degrees and 150 degrees. In some embodiments, one or more engaging members may be perpendicular to the central member.

In some embodiments, the one or more engaging members 280 may extend perpendicularly in one or both sides of the central member 240 so as to be perpendicular with respect to the central member 240 and/or the first section 210 and the second section 220. In some embodiments, the one or more engaging members 280 may be configured to extend relative to the central member 240.

In some embodiments, each engaging member 280 may include a first end 281 coupled to or disposed on or extending from the central member 240 on either the first portion 250 and/or the second portion 260, an opposing second end 283 and a length there between. The opposing, second end 283 may extend from the central member 240 and may be considered a "free end".

In some embodiments, the device 100 may include a first set 284 of one or more engaging members disposed on or extending from the first portion 250 and a second set 286 of one or more engaging members disposed on or extending from the second portion 260. In some embodiments, the device 100 may include one set of one or more engaging members, the first set 284 or the second set 286, disposed only on or extending from one portion (e.g., the first portion or the second portion) of the leaflet section and/or extending from one side of central member 240 disposed in that portion.

In some embodiments, each set 284, 286 of one or more engaging members 280 may include any number of engaging members. In some embodiments, each set 284, 286 of one or more engaging members 280 may include one or more engaging members having a same and/or different dimensions (e.g., length, width, etc. relative to the central portion) and/or shape.

In some embodiments, each set of one or more engaging members 280 may be symmetric relative to the central member 240, as shown in the FIGS. 1-2F. For example, the one or more engaging members 280 may have the same shape and length, and disposed to extend from the same position relative to the first portion 250 and/or second portion 260 in opposing directions. In some embodiments, the one or more engaging members 280 disposed on a portion of the central member 240 may be offset relative to the direction.

For example, the one or more engaging members 280 may have an elongated shape with a free end. In some embodiments, the one or more engaging members 280 may be a barb, teeth, among others, or a combination thereof. In some embodiments, the one or more engaging members 280 may have a smooth surface and/or textured surface that is configured to face the native leaflet.

In some embodiments, each set of engaging member(s) 284, 286 may be disposed in a pattern. For example, the first set 284 may include one or more rows of engaging members 280 that are disposed in parallel to each other and are symmetric with respect to the central member 240. Each row of the first set 284 may be spaced apart by a distance 285 relative to the central member 240. The second set 286 may include one or more rows of engaging members 280 that are disposed in parallel to each other and are symmetric with respect to the central portion. Each row of the second set 286 may be spaced apart by a distance or space 287. In some embodiments, the distance 285 and 287 between each row of a set and/or between each set may be substantially the same as shown in FIGS. 2A-2F. In some embodiments, the distance may be different and/or varied.

In some embodiments, the one or more rows of engaging members 280 of the first set 284 and/or the second set 286 may be disposed offset relative to the central member 240.

As shown in the figures, the first set of engaging members 284 may be disposed offset to the second set 286 of the engaging members with respect to the central portion 270. The first set of engaging members 284 and the second set of engaging members 286 may be disposed in a pattern in which the engaging members of each set is spaced by the distance 285 and 287, respectively. The distance 285 and 287 may correspond to the width of the engaging member. By offsetting the first set 284 and the second set 286, the engaging members can better cover the surface area of the leaflet resulting in improved attachment of the leaflet section to the native leaflet.

In some embodiments, the second set 286 may include more engaging members than the first set 284. By way of example, the second set 286 may include four rows of engaging members 280 and the first set 284 may include three rows of engaging members 280, as shown in FIG. 2A-F. In another example, each set may include more or less engaging members. In a further example, the second set 286 may include the same number of engaging members and/or less engaging members as the first set 284.

In some embodiments, the first set 284 and/or the second set 286 may include different engaging members and/or different pattern of engaging members. For example, the first set 284 and/or the second set 286 may include one or more engaging members that have a different size (e.g., length and/or width) and/or shape, one or more that are not symmetric with respect to the central member 240, among others, or a combination thereof. For example, the first set 284 and/or the second set 286 may include one or more rows of engaging members that has different size and/or width from one or more row(s) in the respective set or the other set.

In some embodiments, the rows of one or more engaging members 280 may extend from the central member 240 linearly, for example, as shown in FIGS. 2A-2F. In some embodiments, the one or more engaging members 280 may include a curvature relative to the central member 240. In some embodiments, the one or more engaging members 280 may include a curved segment and a substantially straight segment. For example, the curved segment may extend from the central member 240 and the straight segment may include the free end so that the trailing edge of each engaging member may be straight.

Figure 6A:
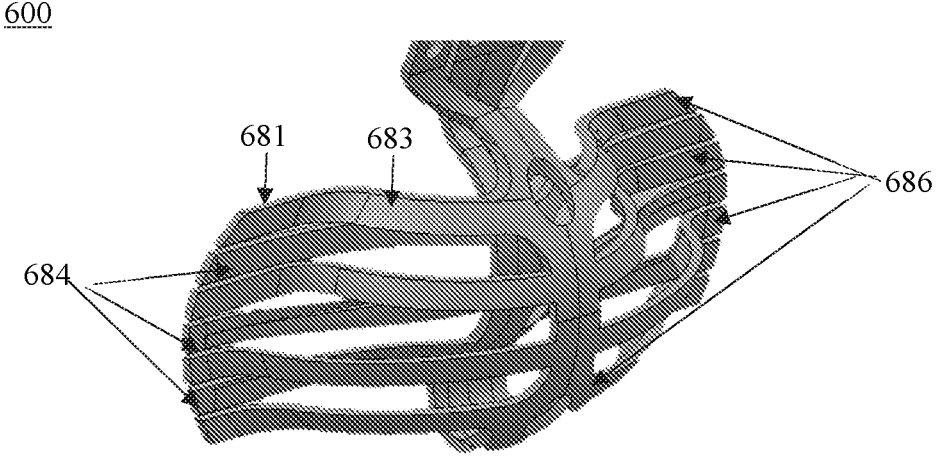
FIGS. 6A and 6B show views of a leaflet section according to some embodiments.
Figure 6B:
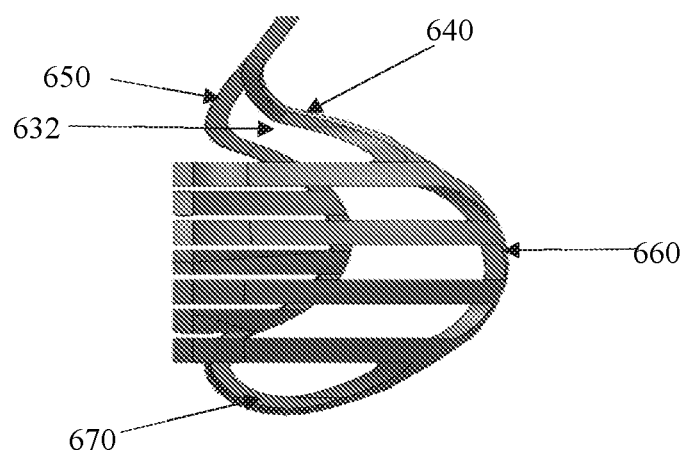

FIGS. 6A and 6B show views of an example of a leaflet section 630 including engaging members 680 that have a curvature segment and a linear segment so that they have a "wing-like" shape. In some embodiments, the leaflet section 630 may include a central member 640. Like the central member 240, the central member 640 may include a first portion 650, a second portion 650, and a base portion 670. The leaflet section 630 may include a first set 684 of rows of engaging members extending from the first portion 650 and a second set 686 of rows of engaging members extending from the second portion 660. In this example, the first set 684 may include less rows than the second set 686 and the rows of each set may be disposed to alternate like the engaging members 280. Each engaging member of the first and second sets 684 and 686 may include a curvature segment that extends from the respective portion and a linear segment that includes the free end. Each engaging member of the first set 684 may include a curvature segment with a different amount of curvature than each engaging member of the second set 686. For example, the set 684 may include a larger outward radius of curvature closer to the central member 240 and taper to a flatter segment at their distal (e.g., free) ends, which is closer to the leaflet surface. The central member 640 and sets 684 and 686 of engaging members may be configured to define a leaflet region 632 in which a native leaflet may be disposed.

In some embodiments, as shown in FIGS. 2A-F, the first section 210 may be disposed to extend from the first end 241 of the leaflet section 230 and the second section 220 may be disposed to extend from the second end 243 of the leaflet section 230. In this example, the first section 210 and the second section 220 may extend from opposite sides of the leaflet section 230 (e.g., the central member 240). In this example, the first section 210 may be considered an extension of the first portion 250 (or the ventricular side or section) and the second section 220 may be considered an extension of the second portion 260 (or the atrial side or section).

In some embodiments, the first section 210 and the second section 220 may have the same or different size and/or shape. In some embodiments, the first section 210 or the second section 220 may be larger than the other section. In some embodiments, the larger section may include an opening disposed therein so that the smaller section may be disposed substantially planar with the larger section. In some embodiments, the second section 220 may be larger than the first section 210 and include an opening 226 so that the first section 210 may be disposed within the opening 226 of the second section. The opening 226 may also provide one or more surfaces for tissue to grow into and across the sections when implanted. As shown in the Figure-2E, the first section 210 and the second section 220 may be disposed to be aligned or biased so that the first section 210 and the second section 220 are coplanar. As shown in FIG. 2E, the first section 210 and the second section 220 may be substantially aligned with planar P profile or axis.

In some embodiments, at least a portion of the first section 210 may be disposed to bend or be biased towards the second section 220 and/or the second portion 260, and/or at least a portion of the second section 220 may be disposed to bend or be biased towards the first section 210 and/or the first portion 250 so that a portion of the first section 210 and second section 220 cross, overlap, among other things, or any combination thereof.

In some embodiments, the first section 210 and/or the second section 220 may include one or more openings configured to provide surfaces into which tissue may grow and/or promote tissue growth across the first section 210 and/or the second section 220.

In some embodiments, the first section 210 and the second section 220 may have an elongated shape. In some embodiments, each of the first section 210 and the second section 220 may have substantially the same width along the length. In some embodiments, the first section 210 and the second section 220 may include a tapered portion 214 and 224, respectively, disposed adjacent to the respective end of the leaflet section 230. In some embodiments, the tapered portion may have a width that is smaller than the central member 240. Each section may have substantially the same width from the tapered portion and have a rounded surface at the top or end of each section.

In some embodiments, the body 200 may be machined from a single sheet or block of a material, such as a metal, polymer or plastic or any other material or machined from a block of material. For example, the device may be made of a shape memory alloy (e.g., Nitinol). If machined from a single sheet of material, a flat skeleton or frame of the device may be cut to the desired dimensions and the resulting flat skeleton may be bent into a three dimensional final (closed configuration) configuration. The final configuration may be permanently set or may be set with techniques such that when the device is deformed out of its final configuration, it may spring back to the final configuration when the deforming forces on the device are removed. In some cases, the final configuration may be achieved by mechanical bending of the flat skeleton into the three dimensional shape, without the ability to deform the final configuration. If the device were to be machined from a block of material, then the final three dimensional configuration may be directly achieved without machining the flat skeleton and bending it into a 3D configuration. Using other techniques, the final configuration of the device may be achieved by building layer on layer of the material. Machining the device may not be limited to these techniques, and other techniques to achieve the final configuration may be used.

FIG. 2F shows the flat frame of the body 200 from which the body 200 shown in FIGS. 1A-2E and can be made. In some embodiments, the flat frame may be made of a shape memory material (e.g., Nitinol), metals, biocompatible materials, among others, or a combination thereof. For example, the default configuration of the device can be determined and set at the time of machining, shape setting or later. For example, the three-dimensional shape of the leaflet section (e.g., the amount of curvature) and the positioning of the first section relative to the second section may be set.

In some embodiments, the device may be machined or shape set so that the default configuration includes the first section being disposed to bend towards the second section, or the second section being disposed to bend towards the first section, such that the first and second sections are close to each other, or touch each other or cross each other. In the configuration where the two sections are close to each other, the space between them may be smaller than the thickness of the native leaflet. In the configuration where first and second sections touch or cross each other, the extent of their touching or crossing provided in the default configuration can be determined and set at the time of machining, shape setting or later.

In some embodiments, the device 100 may include one or more tissue gripping members disposed to protrude from the inner (facing) surface 211 of the first section 210 and/or the inner (facing) surface 221 of the second section 220. The inner surfaces 211 and 221 correspond to the surface of the leaflet that will directly oppose and attach to the native leaflet. In some embodiments, the first section 210 and the second section 220 may include one or more coupling members configured to receive attachment plate (s) as well as other accessory members.

In some embodiments, the one or more tissue gripping members may be disposed on one or more plates that can be attached to the inner surfaces 211 and/or 221. The plate may be attached to the surfaces 211 and/or 221 via coupling members 204, for example, using a fastener such as a suture.

In some embodiments, the device may include one or more plates that include one or more gripping members for one or more portions of the device. In some embodiments, the device may include a plate that includes one or more gripping members for each surface.

FIGS. 1A and B show an example of the device 100. As shown in FIGS. 1A and B, the device 100 may include a plate 300 disposed on the inner surface 211 and a plate 400 disposed on the inner surface 221 of the body 200.

FIGS. 3 and 4 show the plates 300 and 400 that can be configured to respectively be attached to the inner surface 211 of the first section 210 and the inner surface 221 of the second section 220.

Figure 3A:
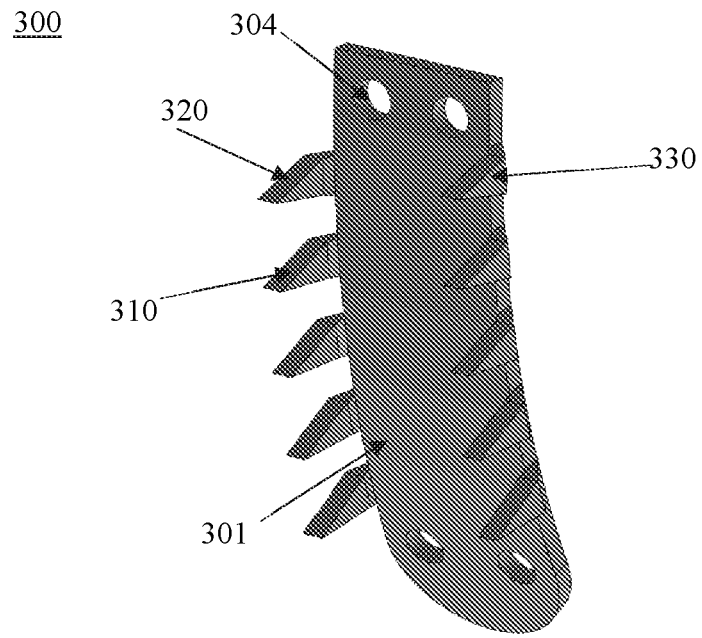
FIGS. 3A and B show views of one of the plates shown in FIGS. 1A and B.
Figure 3B:
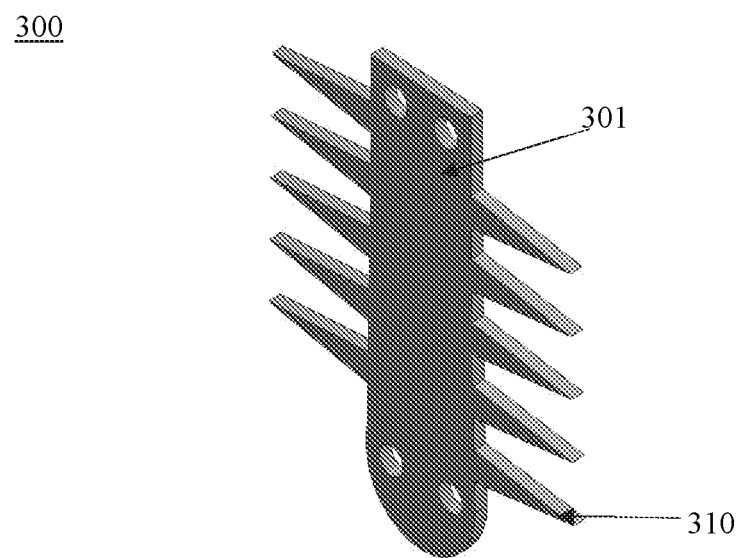

FIG. 3A shows the plate 300 that is configured to be disposed on the inner surface 211 and FIG. 3B shows the flat sheet of material, such as a shape memory material (e.g., Nitinol), from which the plate 300 shown in FIG. 3A may be machined. As shown in FIG. 3A, the plate 300 may include one or more tissue gripping members 310 disposed to protrude from a surface 301. In this example, the one or more tissue gripping members 310 may include two columns 320 and 330 of tissue gripping members disposed on opposite sides or edges of the plate 300. In some embodiments, the one or more tissue gripping members 310 may be disposed in a different pattern (e.g., one column, plurality of rows), disposed at different positions, have a different shape, have a different size, among others, or a combination thereof. The plate 300 may be attached to the first section 210 via one or more coupling members (e.g., openings) 304 so that the surface 301 and the tissue gripping members 320 and 330 can contact and attach to the respective leaflet tissue.

Figure 4A:
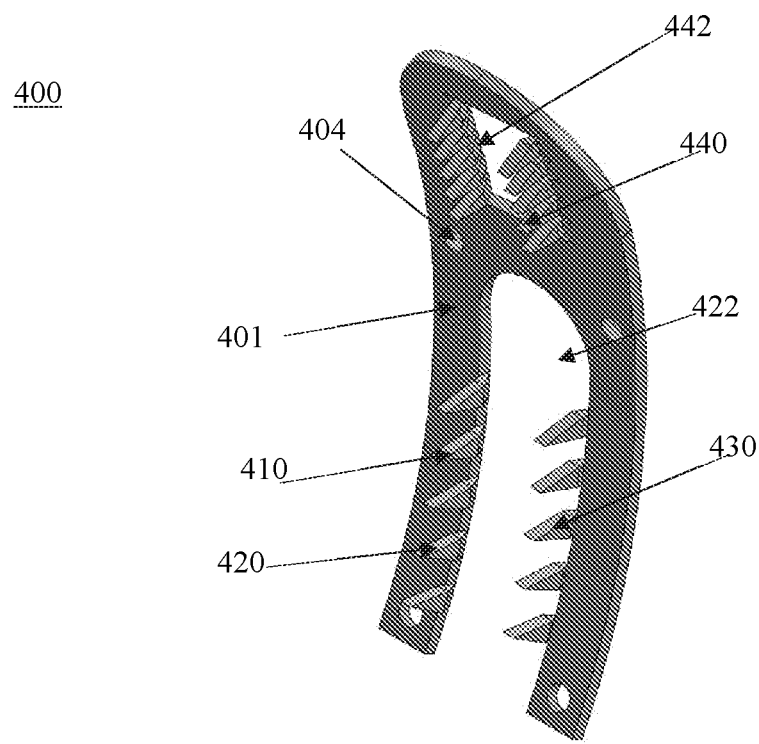
FIGS. 4A and 4B show views of another one of the plates shown in FIGS. 1A and B.
Figure 4B:
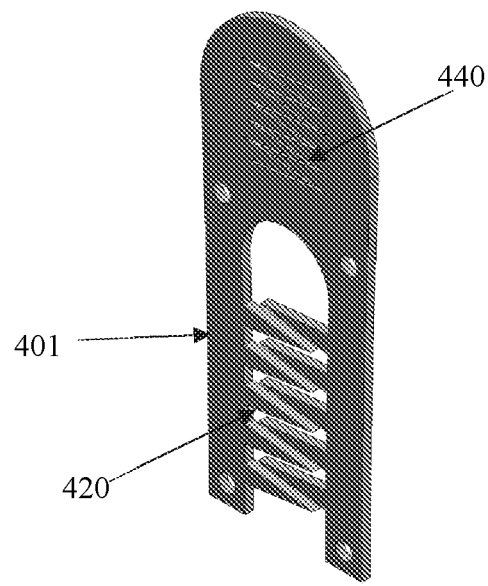

FIG. 4A shows the plate 400 that is configured to be disposed on the inner surface 311 and FIG. 4B shows the flat sheet of material, such as Nitinol, from which the plate 400 shown in FIG. 4A may be machined. As shown in FIG. 4A, the plate 400 may include one or more tissue gripping members 410 disposed to protrude from a surface 401. Like the second section 220, the plate 400 may include an opening 422 that corresponds to the opening 222.

In this example, the one or more tissue gripping members 410 may include two columns 420 and 430 of tissue gripping members disposed on opposite sides or edges of the opening 422. In some embodiments, the plate 400 may include one or more tissue gripping members 440 disposed on opposite sides or edges of the opening 442. The openings 422 and 442 can provide surfaces for tissue to grow into and across the first section 210 and/or the second section 220. In some embodiments, the body 400 may include additional or different structures to promote tissue growth.

In some embodiments, the one or more tissue gripping members 410 may be disposed in a different pattern (e.g., one column, plurality of rows), disposed at different positions, have a different shape, have a different size, among others, or a combination thereof. The plate 400 may be attached to the second section 220 via one or more coupling members (e.g., openings) 404 so that the surface 401 and the tissue gripping members 410 can contact and attach to the respective leaflet tissue.

In some embodiments, the one or more tissue gripping members 310 and/or 410 may be integrated with the inner facing surface 211 and/or the inner facing surface 221. For example, the one or more tissue gripping members 310 and/or 410 may be made from the flat sheet of material from which the body 200 is machined.

Figure 17A:
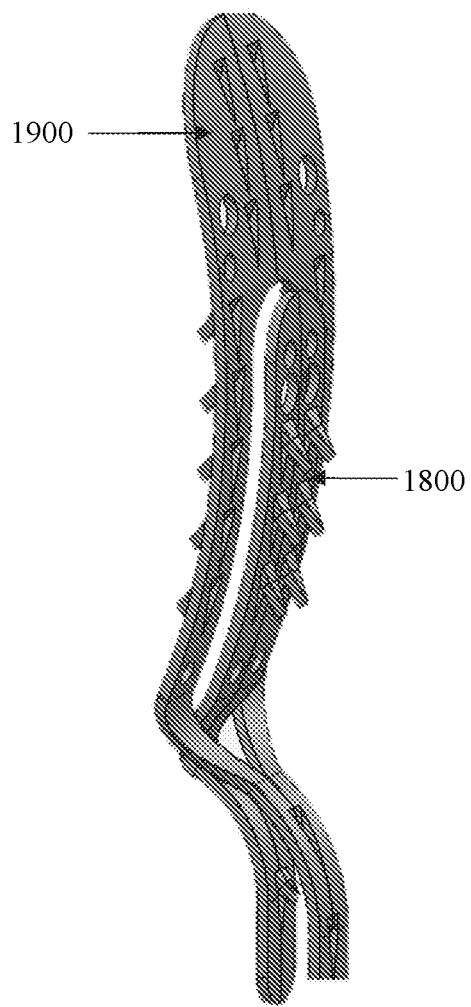
FIGS. 17A and B show views of the plates shown in FIGS. 16A and B.
Figure 17B:
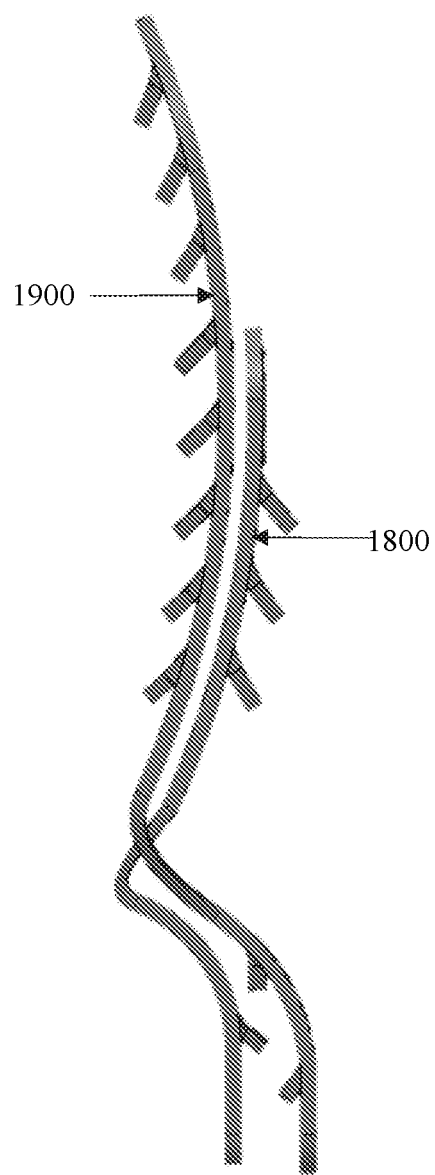

In some embodiments, the one or more plates may be configured to extend within the leaflet section of the device body. FIGS. 16A and 16B shows views of an example of a device 1600. In some embodiments, the device 1600 may include more than one plate attached to the device body. As shown in FIGS. 16A and 16B, the device 1600 may include a first plate 1800 and a second plate 1900 that are attached to the inner facing surface 211 and the inner facing surface 221, respectively, of the device body 200 and that extend within the region 232 of the leaflet region 230. FIGS. 17A and 17B show views of the plates 1800 and 1900, respectively, isolated from the device body 200, shown in FIGS. 16A and 16B.

Figure 18:
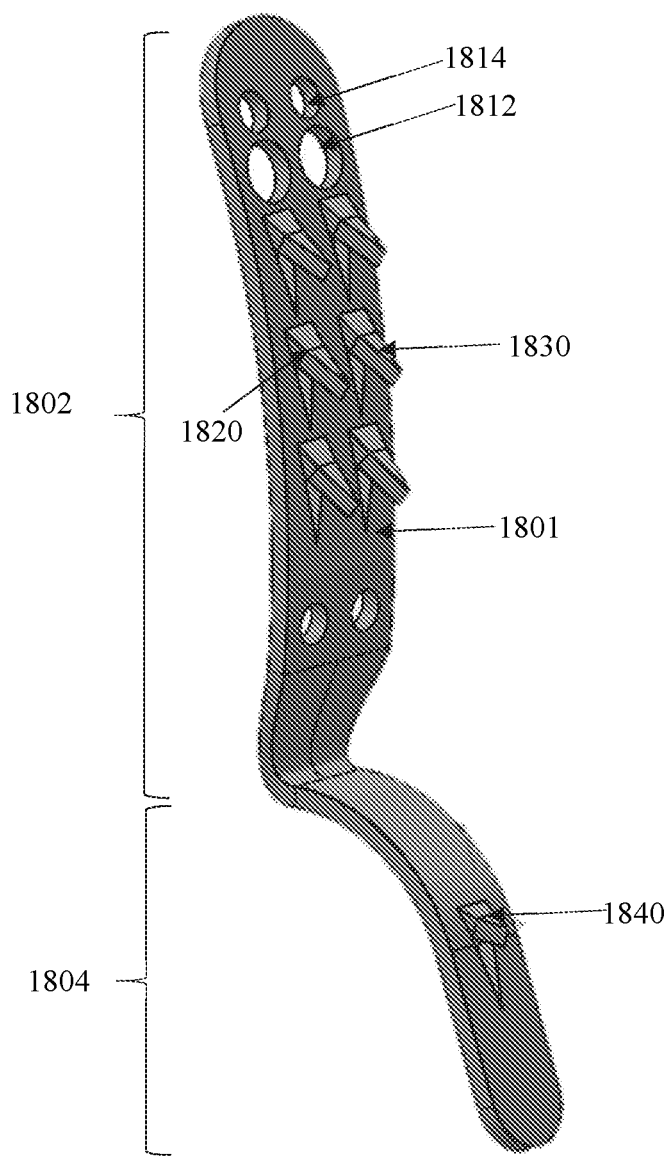
FIG. 18 shows a view one of the plates shown in FIGS. 16A-17B.

In some embodiments, FIG. 18 shows the plate 1800 that can be configured to be disposed on the inner surface 211.

As shown in FIGS. 16A-18, the plate 1800 may include one or more sections. In some embodiments, the plate 1800 may include a first section 1802 configured to attach to the inner surface 211 of the first section 210 and a second section 1804 configured to partially extend into the region 232 of the leaflet section 230 when the plate 1800 is attached. The first section 1802 may extend in a direction at a first angle and the second section 1804 may extend in a direction at a second angle that is different from the first angle.

Like the plate 300, the plate 1800 may include one or more openings 1812 (coupling members) configured to attach the surface 211, one or more openings 1814 configured to provide surface(s) for tissue to grow into and across the device 200, among others, or a combination thereof. In some embodiments, the coupling members 1812 may be different and may be complementary to the one or more coupling members of the device 200. In some embodiments, the body 1800 may include additional or different structures to promote tissue growth.

In some embodiments, the plate 1800 may include one or more tissue gripping members 1810 disposed to protrude from a surface 1801. In this example, the one or more tissue gripping members 1810 may include one or more sets of one or more gripping members disposed in the first section 1802 and/or the second section 1804.

In some embodiments, the one or more tissue gripping members 1810 may include a first set of gripping members 1820 disposed in a column and a second set of gripping members 1830 disposed in a column. The first set 1820 and the second set 1830 of tissue gripping members may be disposed on opposite sides or edges of the first section 1802. In some embodiments, the plate 1800 may include a set 1840 of one or more tissue gripping members 1810 disposed on the surface 1801 of the second section 1804.

In some embodiments, the one or more gripping members 1810 may have a pointed shape (e.g., teeth) and project from the surface 1801 towards the second section 1804 (or leaflet section 230 when attached). The gripping members 1810 are not limited to this shape and may have a different shape including but are not limited to barbs, other projections, among others, or a combination thereof.

In some embodiments, the plate 1800 may include a different number of gripping members 1810 within each set, different number of sets of gripping members, among others, or a combination thereof. In some embodiments, the one or more tissue gripping members 1810 may be disposed in a different pattern (e.g., one column, plurality of rows), disposed at a different position, have a different shape, have a different size, among others, or a combination thereof.

Figure 19:
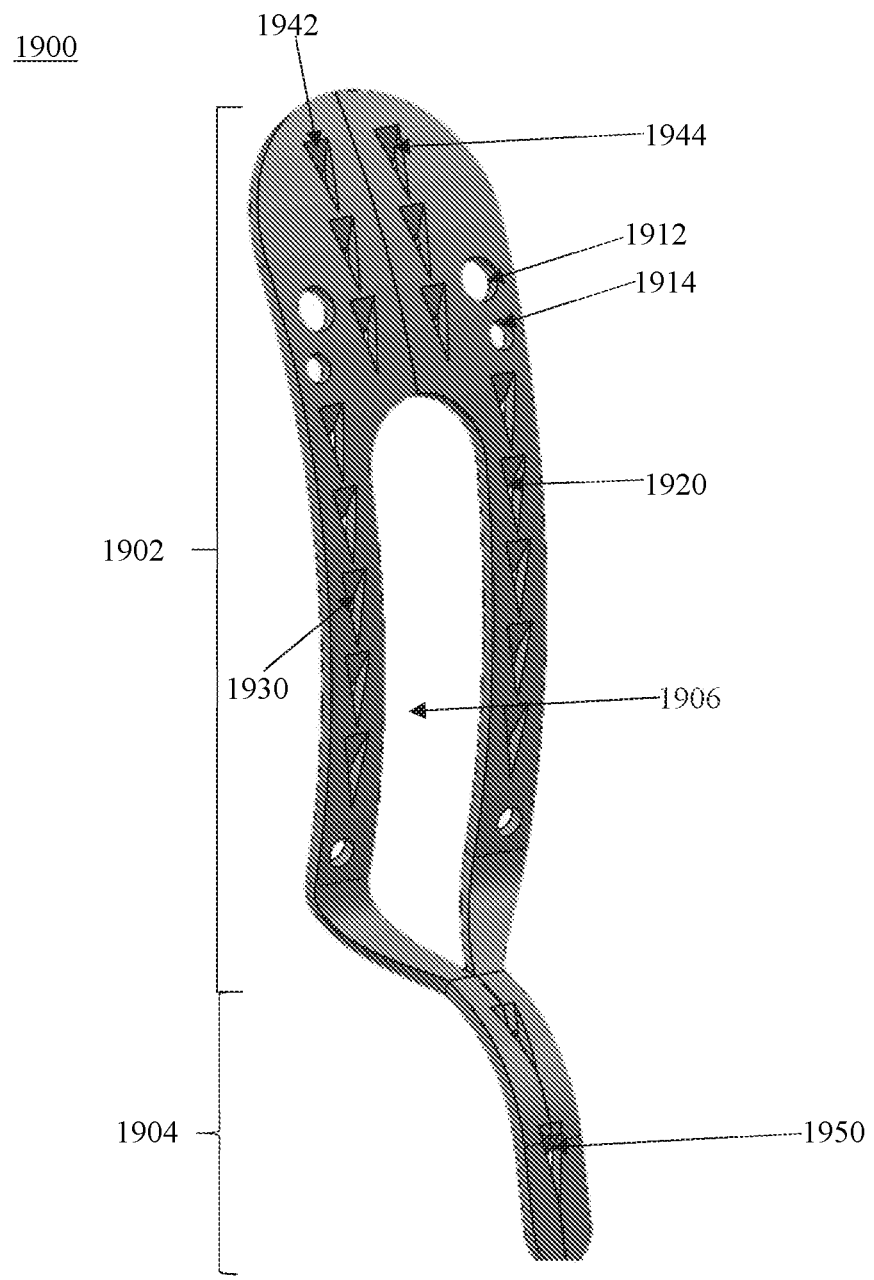
FIG. 19 shows a view of the other plate shown in FIGS. 16A-17B.

Like plate 1800, the plate 1900 may include a section that is configured to at least partially extend within the leaflet section 230. FIG. 19 shows the plate 1900 that is configured to be disposed on the inner surface 221. As shown in FIGS. 16A-17B and 19, the plate 1900 may include one or more sections. In some embodiments, the plate 1900 may include a first section 1902 configured to attach to the inner surface 221 of the second section 220 and a second section 1904 configured to partially extend into the region 232 of the leaflet section 230 when the plate 1900 is attached. The first section 1902 may extend in a direction at a first angle and the second section 1904 may extend in a direction at a second angle that is different from the first angle.

Like the plate 400, the plate 1900 may include one or more openings 1912 (coupling members) configured to attach the surface 221, one or more openings 1914 configured to provide surface(s) for tissue to grow into and across the device 200, among others, or a combination thereof. In some embodiments, the coupling members 1912 may be different and may be complementary to the one or more coupling members of the device 200. In some embodiments, the body 1900 may include additional or different structures to promote tissue growth.

Like the second section 220, the plate 1900 may include an opening 1906 disposed in the first section 1902 that corresponds to the opening 222. In some embodiments, the plate 1900 may include one or more tissue gripping members 1910 disposed to protrude from a surface 1901. In this example, the one or more tissue gripping members 1910 may include one or more sets of one or more gripping members disposed in the first section 1902 and/or the second section 1904.

In this example, the one or more tissue gripping members 1910 may include one or more sets of one or more tissue gripping members 1910. In some embodiments, the one or more tissue gripping members 1910 may include one or more sets disposed along the first section 1902 surround the opening 1906. In some embodiments, the one or more gripping members 1910 may include a first set 1920 disposed in a column and a second set 1930 disposed in column. The first set 1920 and the second set 1930 of gripping members may be disposed on opposite sides or edges of the opening 1906. In some embodiments, the plate 1900 may include one or more sets of gripping members 1910 disposed above the opening 1906. In some embodiments, the one or more gripping members 1910 may include a first set 1942 and a second set 1944 disposed in adjacent columns and above the opening 1906.

In some embodiments, the plate 1900 may include a set 1950 of one or more tissue gripping members 1910 disposed on the surface 1901 of the second section 1904. In this example, the set 1950 may include two gripping members 1910 disposed in a column.

In some embodiments, the one or more gripping members 1910 may have a pointed shape (e.g., teeth) and project from the surface 1901 towards the second section 1904 (or leaflet section 230 when attached). The gripping members 1910 are not limited to this shape and may have a different shape including but are not limited to barbs, other projections, among others, or a combination thereof.

In some embodiments, the plate 1900 may include a different number of gripping members 1910 within each set, different number of sets of gripping members, among others, or a combination thereof. In some embodiments, the one or more tissue gripping members 1910 may be disposed in a different pattern (e.g., one column, plurality of rows), disposed at a different position, have a different shape, have a different size, among others, or a combination thereof.

In some embodiments, the first sections 1810 and 1910 of the plates 1800 and 1900 may be attached to the first section 210 and the second section 220, respectively, using any fastening means. For example, the plates 1800 and 1900 may be attached to the device body 200 during the manufacturing process (e.g., welding, adhesive, etc.) or during the implantation processing (e.g., suturing). The second sections 1820 and 1920 may not be attached to the device body 200 and may be configured to extend within the leaflet section 230 when attached.

The attachment plates 1800 and 1900 may be configured so as to not interfere with the biased alignment of the first section 210 and the second section 220 when attached, and therefore may not interfere with the biasing force resulting from the first section 210 and the second section 220. In use, when the device 1600 is moved to an open configuration for implantation on a native leaflet, the plates 1800 and 1900 can be positioned such that the native leaflet may be captured between (i) the first section 1802 and the second section 1804 of the first plate 1800; (ii) the first section 1902 and the second section 1904 of the second plate 1900; and (iii) the leaflet section 230. The gripping members 1810 and 1910 may also engage the tissue of the native leaflet captured there between and can cause friction. The downward projection of the gripping members 1810 and 1910 may also not interfere with the native leaflet as it slides between the first plate 1800 and the second plate 1900. After the leaflet is captured, the gripping members 1810 and 1910 may be configured to dig into the native leaflet tissue due to the downward projection.

Figure 20A:
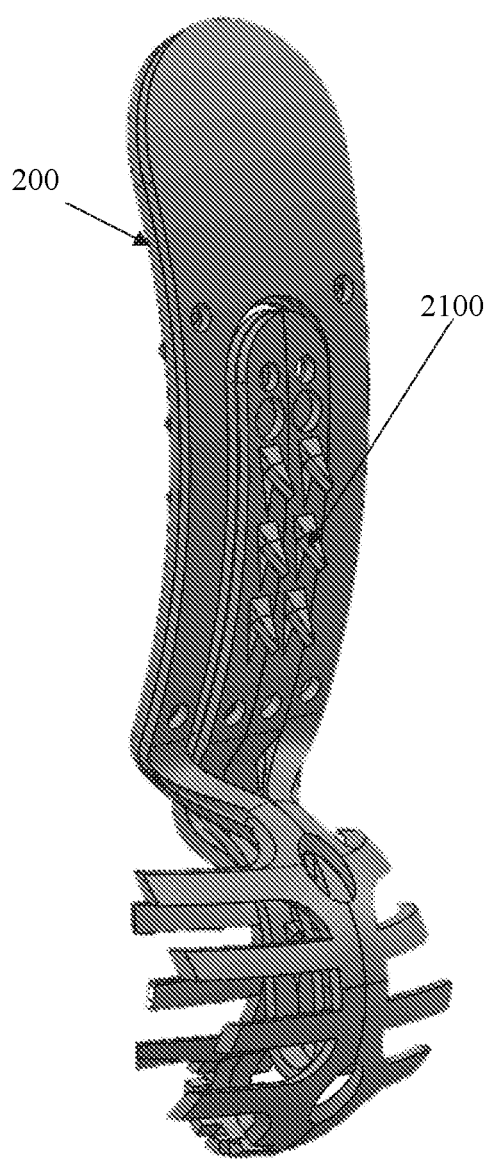
FIGS. 20A and B show views of a leaflet enhancer device according to embodiments.
Figure 20B:
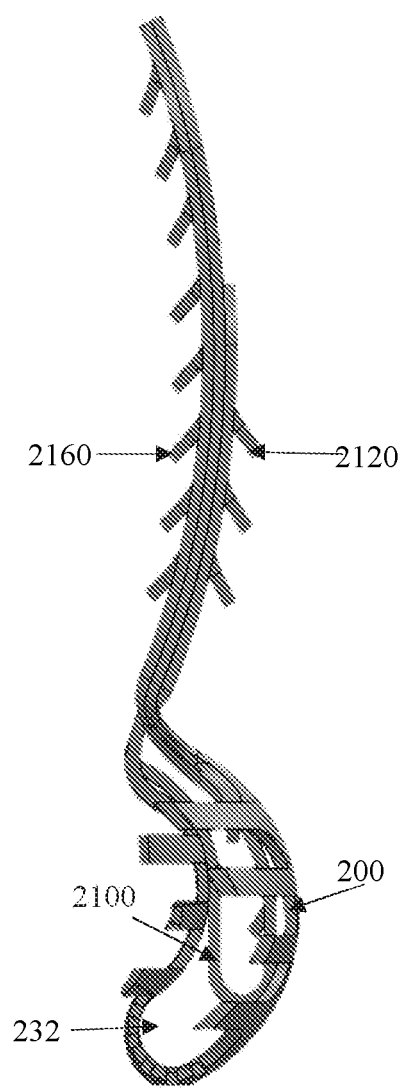
Figure 21A:
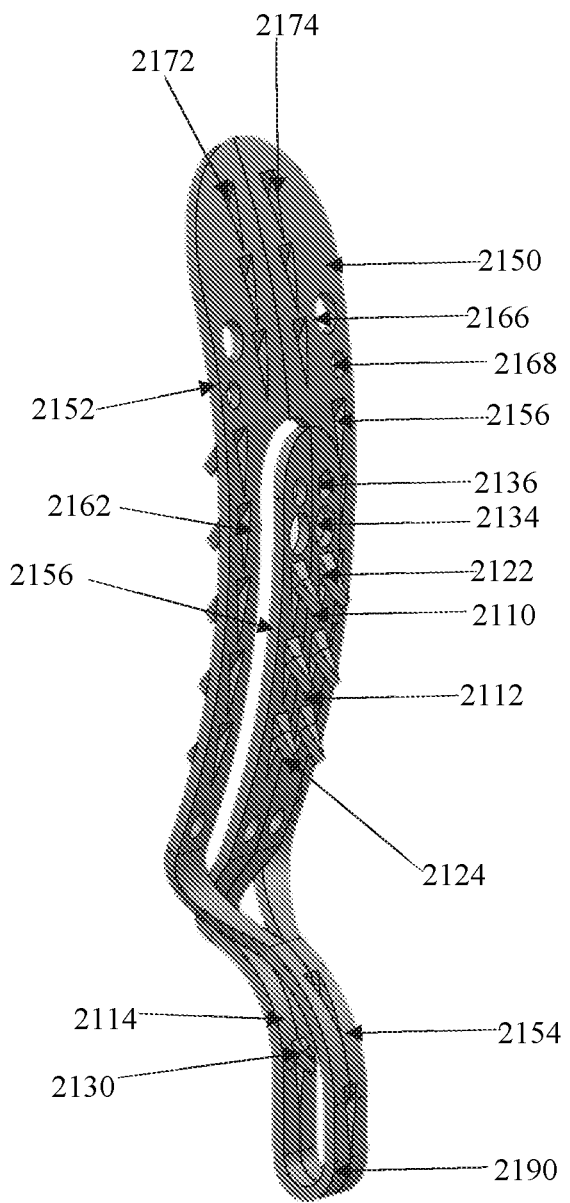
FIGS. 21A and B show views of the plate body shown in FIGS. 20A and B.
Figure 21B:
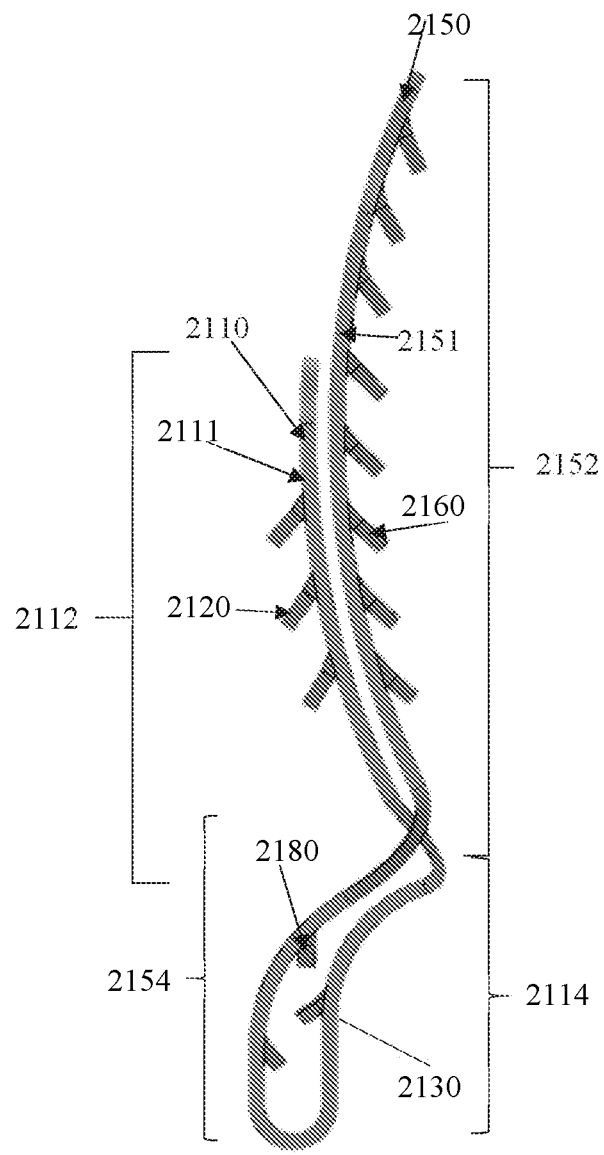

In some embodiments, the attachment plates 1800 and 1900 may be integrated into a single plate body. FIGS. 20A and 20B shows views of an example of a device 2000. In some embodiments, the device 2000 may include a plate body 2100 that can be attached to the inner facing surface 211 and the inner facing surface 221, respectively, of the device body 200 and that extend within the region 232 of the leaflet region 230. FIGS. 21A and 21B show views of the plate body 2100 isolated from the device body 200 shown in FIGS. 20A and 20B.

In some embodiments, as shown in FIGS. 20A-21B, the plate 2100 may include a first plate 2110, a second plate 2150, and a third plate 2190 connecting the first plate 2110 and the second plate 2150. The first plate 2110 may have a similar configuration as plate 1800 and the second plate 2150 may have a similar configuration like plate 1900. The first plate 2110 may be configured to be disposed on the inner surface 211 and the second plate 2150 may be configured to be disposed on the inner surface 221.

Like the plate 1800, the first plate 2110 may include a first section 2112 configured to attach to the inner surface 211 of the first section 210 and a second section 2114 configured to partially extend into the region 232 of the leaflet section 230 when the plate 2110 is attached. The first section 2112 may extend in a direction at a first angle and the second section 2114 may extend in a direction at a second angle that is different from the first angle.

In some embodiments, like the plate 1800, the first plate 2110 may include one or more tissue gripping members 2120 disposed to protrude from a surface 2111. In this example, the one or more tissue gripping members 2120 may include one or more sets of one or more gripping members disposed in the first section 2112 and/or the second section 2114.

In some embodiments, like the plate 1800, the one or more tissue gripping members 2120 may include a first set 2122 of gripping members disposed in a column and a second set 2124 of gripping members 2124 disposed in a column. The first set 2122 and the second set 2124 of tissue gripping members may be disposed on opposite sides or edges of the first section 2112. In some embodiments, the plate 2100 may include a set 2130 of one or more tissue gripping members disposed on the surface 2111 of the second section 2114.

In some embodiments, the one or more gripping members 2120 may have a pointed shape (e.g., teeth) and project from the surface 2111 towards the second section 2114 (or leaflet section 230 when attached). The gripping members 2120 are not limited to this shape and may have a different shape including but are not limited to barbs, other projections, among others, or a combination thereof.

Like plate 1900, the plate 2150 may include a section that is configured to at least partially extend within the leaflet section 230. As shown in FIGS. 20A-21B, the plate 2150 may include one or more sections. In some embodiments, the plate 2150 may include a first section 2152 configured to attach to the inner surface 221 of the second section 220 and a second section 2154 configured to partially extend into the region 232 of the leaflet section 230 when the plate 2150 is attached. The first section 2152 may extend in a direction at a first angle and the second section 2154 may extend in a direction at a second angle that is different from the first angle.

Like the plate 1900, the plate 2150 may include an opening 2156 disposed in the first section 2152 that corresponds to the opening 222. In some embodiments, the plate 2150 may include one or more tissue gripping members 2160 disposed to protrude from a surface 2151.

In this example, the one or more tissue gripping members 2160 may include one or more sets of one or more tissue gripping members 2160 disposed on more one more sections. In some embodiments, the one or more tissue gripping members 2160 may include one or more sets disposed along the first section 2152 surround the opening 2156. In some embodiments, the one or more gripping members 2160 may include a first set 2162 disposed in a column and a second set 2164 disposed in column. The first set 2162 and the second set 2164 of gripping members may be disposed on opposite sides or edges of the opening 2156. In some embodiments, the plate 2150 may include one or more sets of gripping members 2160 disposed above the opening 2156. In some embodiments, the one or more gripping members 2160 may include a first set 2172 and a second set 2174 disposed in adjacent columns and above the opening 2156 as shown in FIG. 19.

In some embodiments, the plate 2150 may include a set 2180 of one or more tissue gripping members 2160 disposed on the surface 2151 of the second section 2154. In this example, the set 2180 may include two gripping members 2160 disposed in a column.

In some embodiments, the one or more gripping members 2160 may have a pointed shape (e.g., teeth) and project from the surface 2151 towards the second section 1904 (or leaflet section 230 when attached). The gripping members 2160 are not limited to this shape and may have a different shape including but are not limited to barbs, other projections, among others, or a combination thereof.

In some embodiments, the plate body 2100 may include a different number of gripping members within each set, different number of sets of gripping members, among others, or a combination thereof. In some embodiments, the one or more tissue gripping members 2120 and/or 2160 may be disposed in a different pattern (e.g., one column, plurality of rows), disposed at a different position, have a different shape, have a different size, among others, or a combination thereof.

Like the plates 1800 and 1900, the plate body 2100 may include one or more openings 2134 and 2166 (coupling members) configured to attach the surfaces 211 and 221, respectively; one or more openings 2136 and 2168 configured to provide surface(s) for tissue to grow into and across the device 200; among others; or a combination thereof. In some embodiments, the coupling members 2134 and 2166 may be different and may be complementary to the one or more coupling members of the device 200. In some embodiments, the body 2100 may include additional or different structures to promote tissue growth.

In some embodiments, the first sections 2112 and 2152 of the plate body 2100 may be attached to the device body 200, using any fastening means. For example, the plate body 2100 may be attached to the device body 200 during the manufacturing process (e.g., welding, adhesive, etc.) or during the implantation processing (e.g., suturing). The second sections 2114 and 2154 may not be attached to the device body 200 and may be configured to extend within the leaflet section 230 when attached.

The plate body 2100 may be configured so as to not interfere with the biased alignment of the first section 210 and the second section 220 when attached, and therefore may not interfere with the biasing force resulting from the first section 210 and the second section 220.

In use, when the device 2000 is moved to an open configuration for implantation on a native leaflet, the plate 2100 can be positioned such that the native leaflet is captured between (i) the first section 2112 and the second section 2114 of the first plate 2110 and (ii) the first section 2152 and the second section 2154 of the second plate 2150. The gripping members 2120 and 2160 may also engage the tissue of the native leaflet captured there between and can cause friction. The downward projection of the gripping members 2120 and 2160 may also not interfere with the native leaflet as it slides between the first plate 2110 and the second plate 2150 toward the connecting plate 2190. After the leaflet is captured, the gripping members 2120 and 2160 may be configured to dig into the native leaflet tissue due to the downward projection.

In some embodiments, the device may include one or more covering members configured to cover at least the outer surface of the leaflet section. As shown in FIGS. 1A and 1B, at least one covering member 500 may be disposed on at least the leaflet section 230. In some embodiments, the device 100 may include additional and/or alternative covering members 500 disposed on other sections and/or configured to be disposed on the leaflet section 230.

In some embodiments, the one or more covering members 500 may partially or completely cover and/or extend beyond the leaflet section 230. In some embodiments, the one or more covering members 500 may be disposed so as to partially extend and cover the first section and/or the second section.

In some embodiments, the one or more covering members 500 may be made of one or more materials. The one or more materials include but is not limited to metal (e.g., wires), a shape memory material, a polymer (e.g., polytetrafluoroethylene (PTFE)), a fabric, a biocompatible material (e.g., felt, PTFE, ePTFE material, decellularized pericardium, synthetic or processed tissue, etc.), among others, or a combination thereof). In some embodiments, the material may be a biocompatible material with or without a polymeric covering (e.g., PTFE). In some embodiments, the material may be flexible.

In some embodiments, the one or more covering members 500 may include woven or braided of the same and/or differential material(s), mesh-like material, one or more layers of the same and/or different material(s) (e.g., a homogenous single layer material or a composite multiple layer material), among others, or a combination thereof. The one or more covering members 500 can be configured to increase the extent of the protrusion or bulge of the leaflet section into the valve orifice the direction of the three dimensional profile (i.e., bulge) of the leaflet section 230. The one or more covering members 500 may also be configured to increase the lateral extent of protrusion or bulge from the leaflet section 220 by extending perpendicularly from the device 200, for example, at least the leaflet section 230, along the native leaflet.

In some embodiments, the material of the one or more covering members 500 may include one or more layers that may be configured to be expandable (e.g., a hydrophilic material that can be configured to absorb blood) after implantation and increase in volume to enhance attachment or compression of the native leaflet between the first and second sections of the device. In some embodiments, the material may enable ingrowth of tissue such that over time a layer of tissue may grow into the device and secure the device better to the native valve leaflet.

Figure 2A:
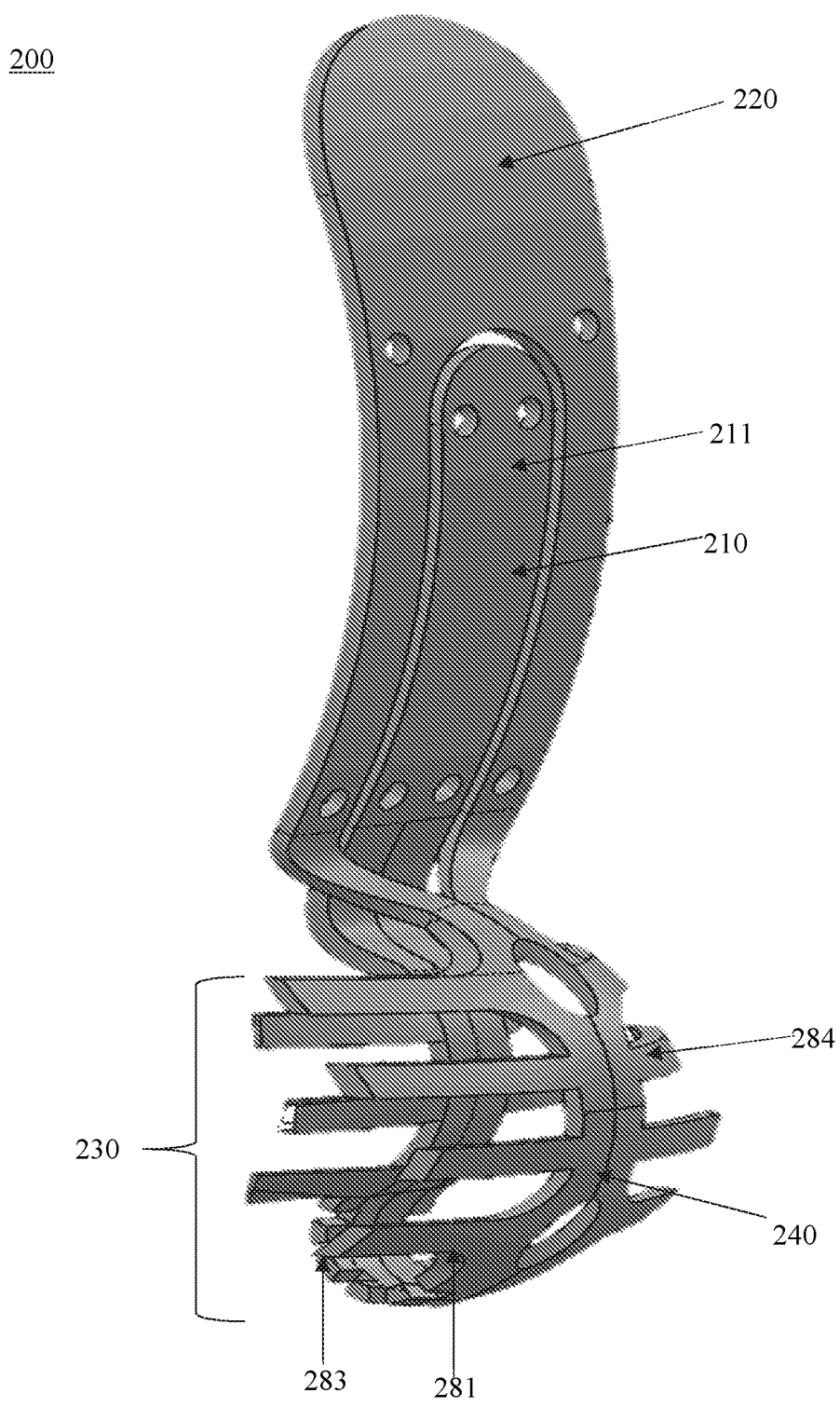
FIGS. 2A-F show views of the body of the device shown in FIGS. 1A and B according to some embodiments.
Figure 2B:
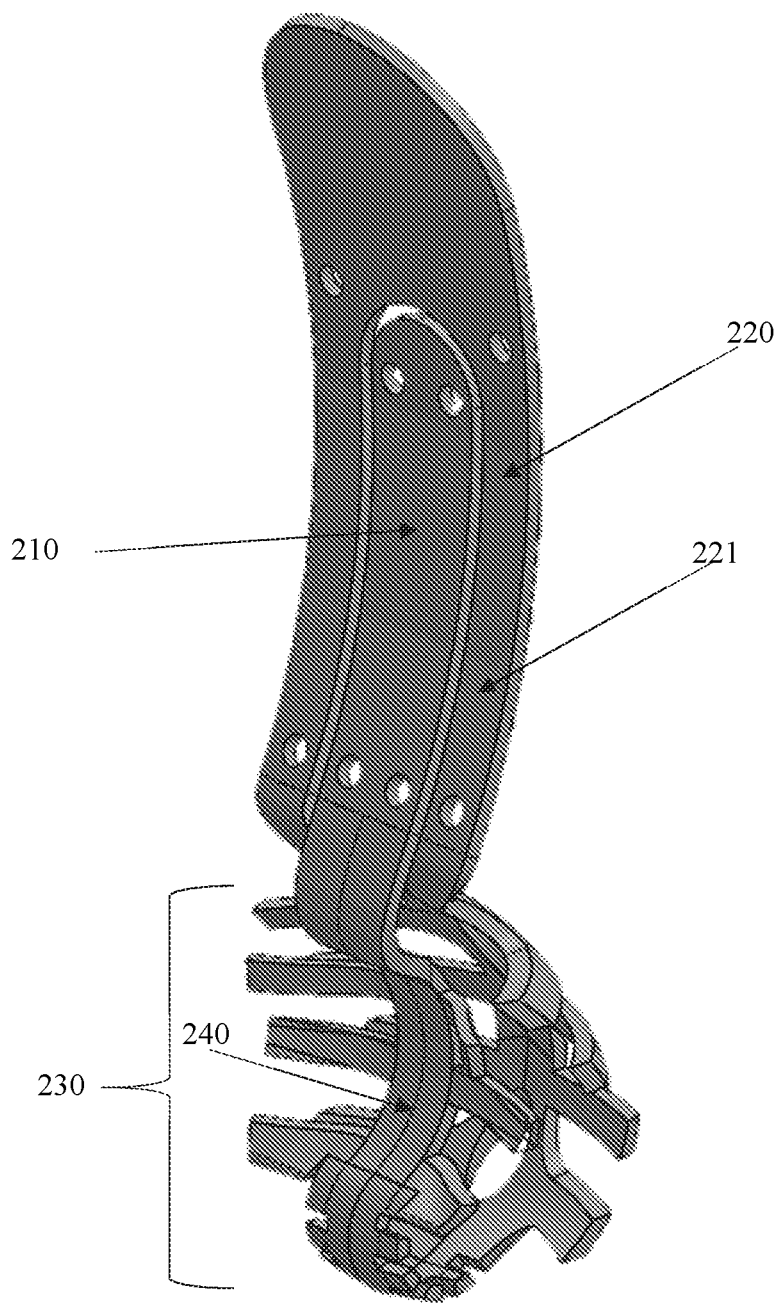
Figure 2C:
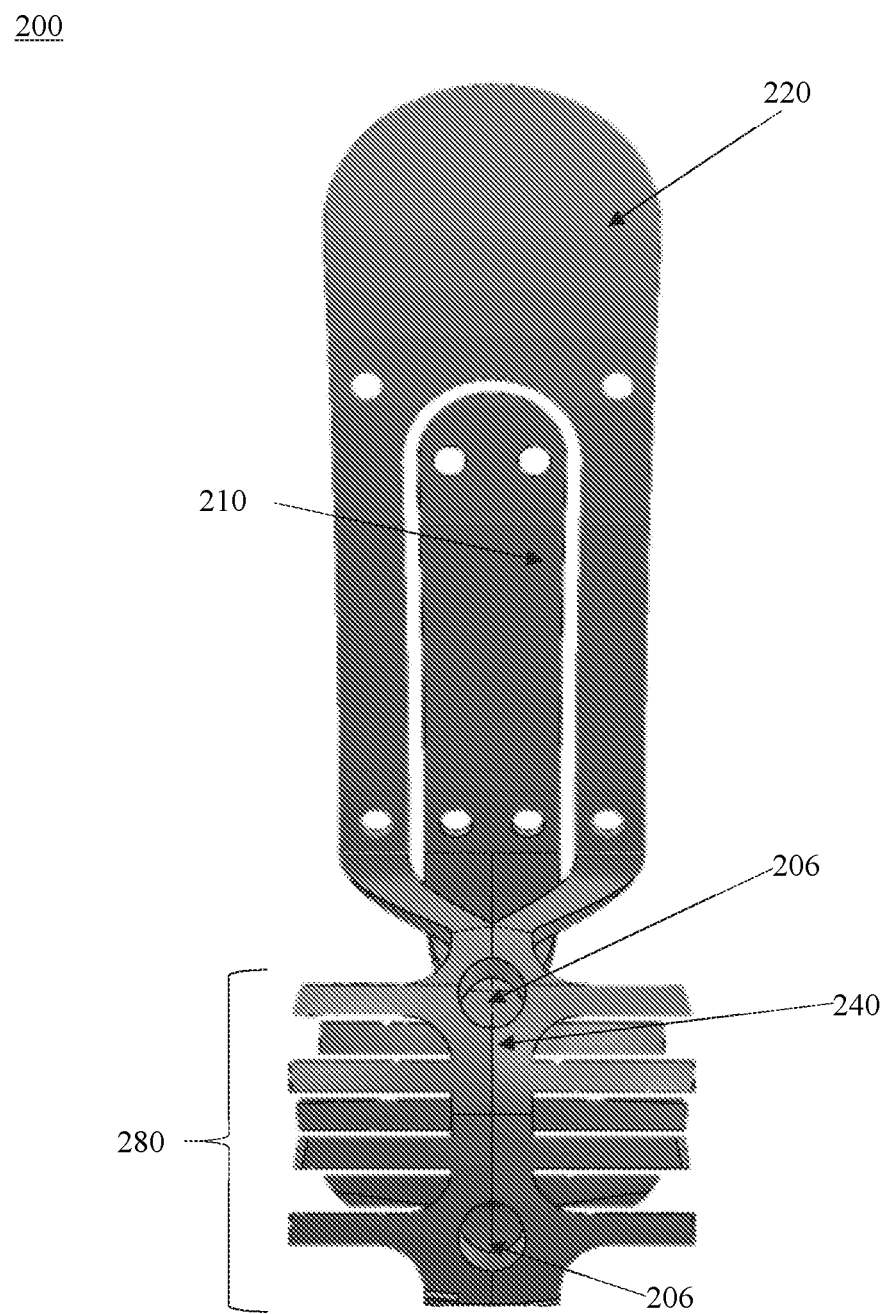
Figure 2D:
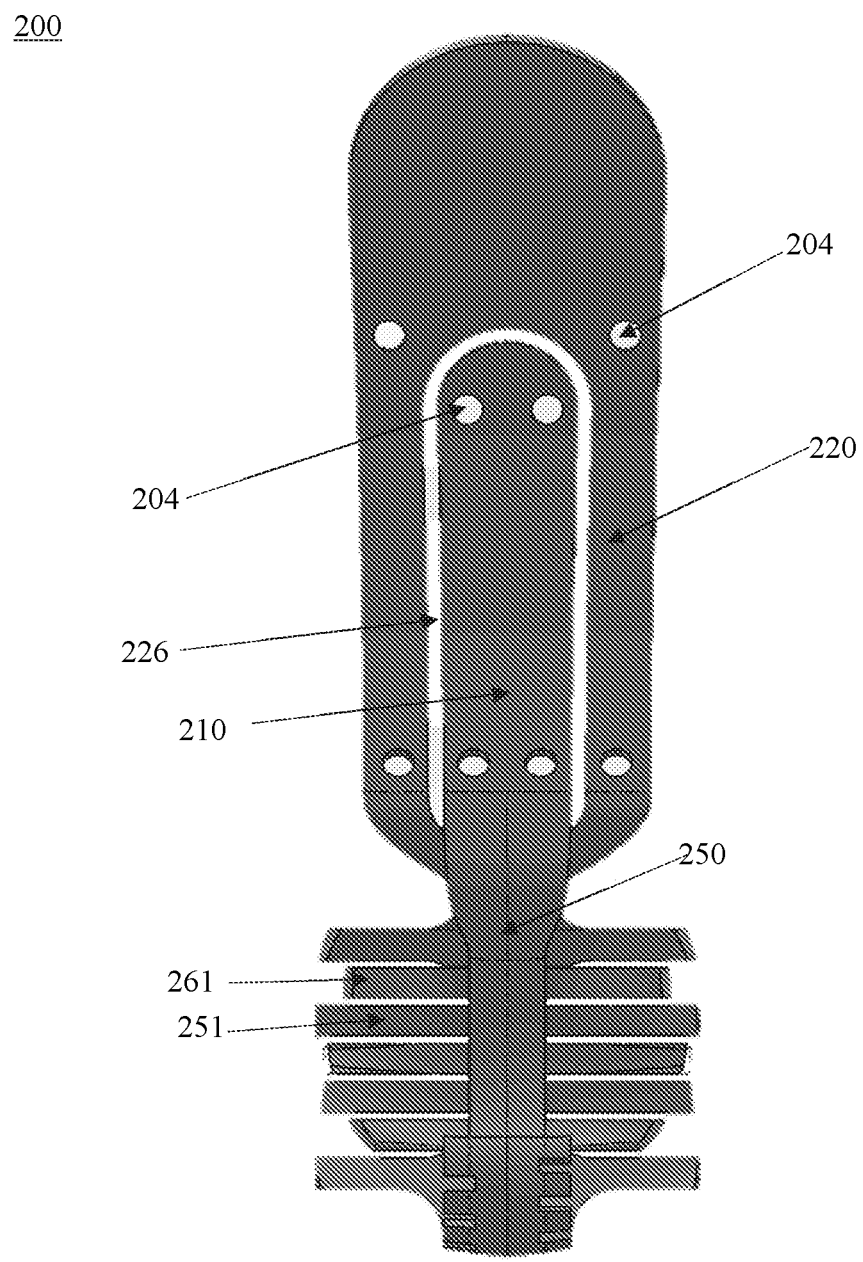
Figure 2E:
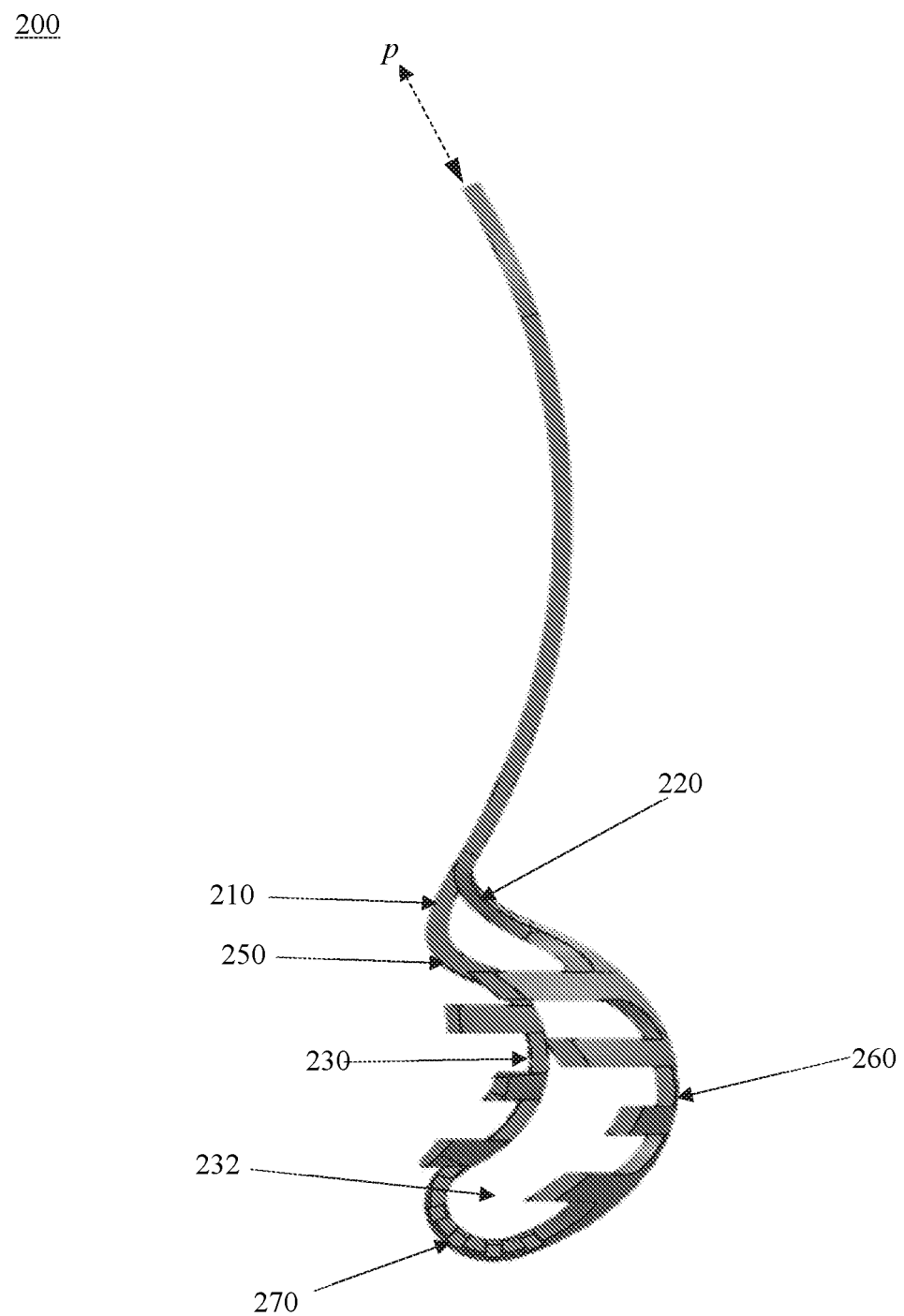
Figure 2F:
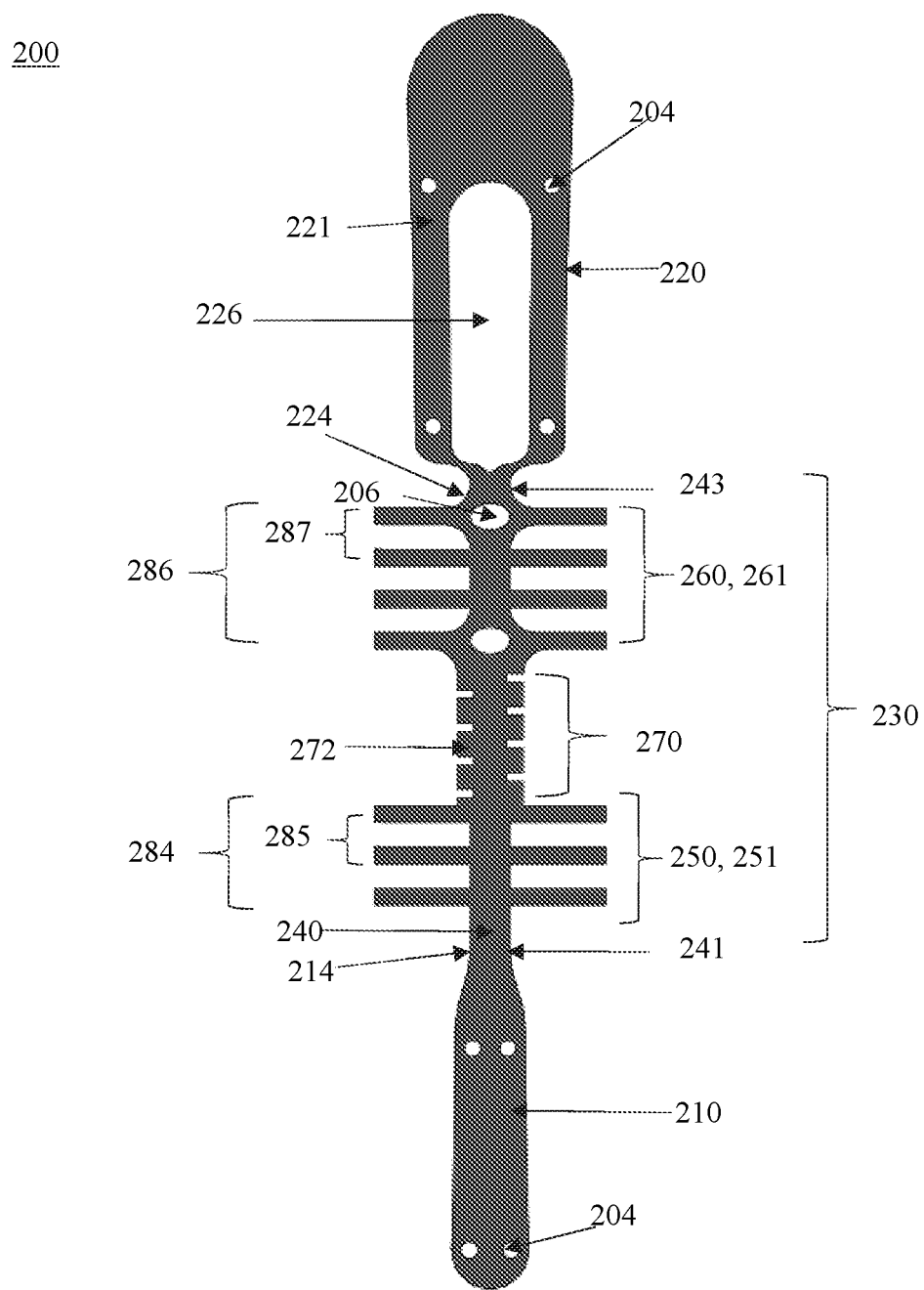
Figure 5A:
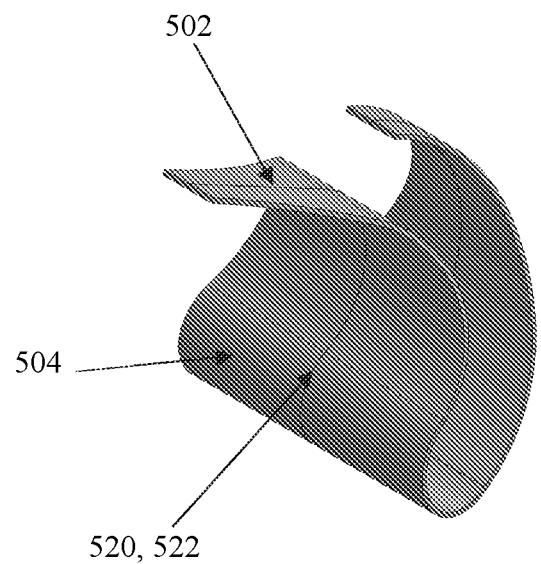
FIGS. 5A and 5B show views of the covering member shown in FIGS. 1 and 2B.
Figure 5B:
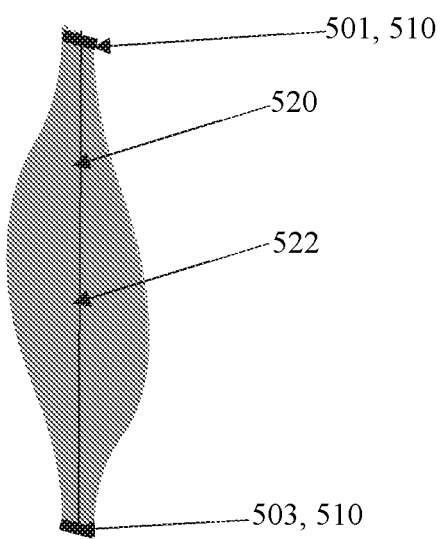

FIG. 5A shows the one or more covering members 500 shown in FIGS. 1A and 2B that is configured to be disposed on at least the leaflet section 230 and FIG. 5B shows the flat sheet of material, such as Nitinol, from which the one or more covering members 500 shown in FIG. 5A may be machined.

In some embodiments, the one or more covering members 500 may be configured to cover or surround or extend beyond the first set 284 of engaging members and/or the second set 286 of engaging members of the leaflet section 230. The one or more covering members 500 may include a curvature corresponding to the leaflet section 230. For example, the region 504 may be configured to cover the leaflet section 230 (e.g., the base portion) and the region 502 may be configured to attach to one surface of the first section 210 and/or the second section 220.

In some embodiments, the one or more covering members 500 may have a first end 501, a second end 503, and a length there between.

In some embodiments, the one or more covering members 500 may include one or more radiopaque metallic elements 510. For example, the one or more radiopaque elements 510 may be disposed at the first end 501 and/or the second end 503. This can identify the location of this structure in relation to the native valve leaflet, so as to enable optimal implantation and delivery with medical imaging.

In some embodiments, the one or more covering members 500 may include a spine 520 that extends along the entire length between the first end 501 and the second end 503. In some embodiments, the spine 520 may be made of a flexible material. In some embodiments, the spine 520 may include a shape memory material so that it can be configured to be bent to a desired shape or permanently shaped set to a desired shape.

In some embodiments, the one or more covering members 500 may include a flexible member 522 disposed along the length of the spine 520. The flexible member 522 may be disposed along entirely or partially along the length of the spine 520. In some embodiments, the flexible member 522 may be an additional layer disposed on the spine 520. In some embodiments, the flexible member 522 may be made of one or more materials or a combination of materials that is different from the spine 520.

In some embodiments, the flexible member may taper along the length of the spine 520. By way of example, the flexible member may have a width that is smaller at the first end 501 and increase towards and till the center of the length of the spine 520; and decrease towards the second end 503.

In some embodiments, the one or more covering members 500 may be configured to be attached to the device 200 by a user and/or during manufacturing. For example, the one or more covering members 500 may include one or more coupling members that can be configured for fastening the cover member 500 to the device body 200 (e.g., leaflet section 230, the first section 210 and/or the second section 220), using, for example, a fastener (e.g., suturing). In some embodiments, the coupling members may include but are not limited to openings, grooves, depressions, among others, or a combination thereof.

In some embodiments, the spine 520 may be configured to be a coupling member enabling attachment of the covering member 500 to the central member 240 of the leaflet section 230 along entirely or partially along the length of the central member 240. In some embodiments, the radiopaque element(s) 510 may also be coupling members. In some embodiments, the covering member 500 may include alternative and/or additional coupling members.

In some embodiments, the one or more covering members 500 may be attached to the leaflet section during manufacturing, for example, by welding.

In some embodiments, the one or more covering members 500 may have different shape. For example, the device 100 may include one or more covering members 500 having dimensions specific to the geometries of the valve defect of the patient. For example, the device 100 may include one or more covering members that have a longer width to address the width of the valve defect (e.g., regurgitant orifice).

Figure 7:
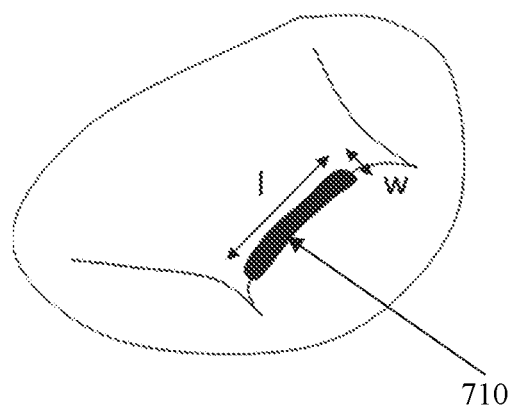
FIG. 7 shows an example of a valve in which the device may be implanted.

By way of example, FIG. 7 shows an example 700 of a regurgitant orifice 710 in which the leaflet enhancer device may be implanted. The dimensions (length and width) of the orifice, may be determined, from medical imaging, such as echocardiography.

Figure 8A:
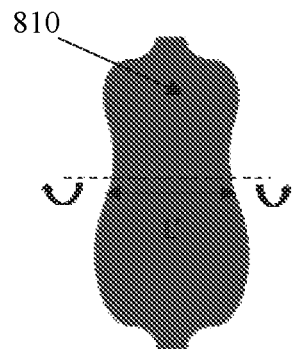
FIGS. 8A-C show views of a device according to some embodiments.

FIGS. 8A-10C show examples of covering members having different lengths, according to some embodiments. FIGS. 8A-8C show a covering member 810 having a length 1.

Figure 8B:
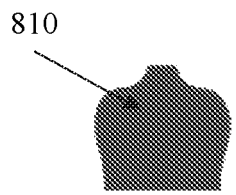
Figure 8C:
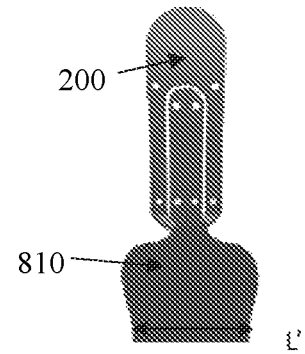

FIG. 8A shows the flat material from which the covering member 810 may be machined, FIG. 8B shows the machined covering member 810 and the FIG. 8C shows the covering member 810 disposed on the leaflet section 230 of the device body 200. The length 1 of the covering member 810 substantially corresponds to the width of the leaflet section that the covering member 810 at least covers the leaflet section 230.

Figure 9A:
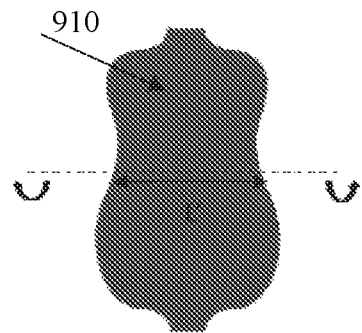
FIGS. 9A-C show views of a device according to some embodiments.
Figure 9B:
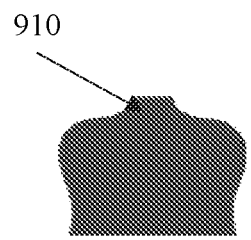
Figure 9C:
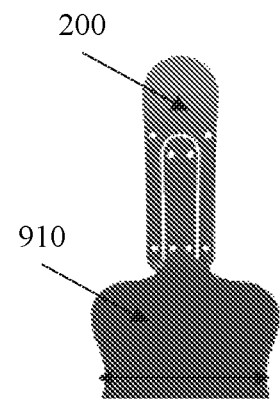

FIGS. 9A-9C show covering member 910 having a length 1 that is longer than the length 1 of the member 810. FIG. 9A shows the flat material from which the covering member 910 may be machined, FIG. 9B shows the machined covering member 910 and the FIG. 9C shows the covering member 910 disposed on the leaflet section 230 of the device body 200. The length 1 of the covering member 910 is longer than the width of the leaflet section 230 so that the covering member 910 covers and extends from the leaflet section 230.

Figure 10A:
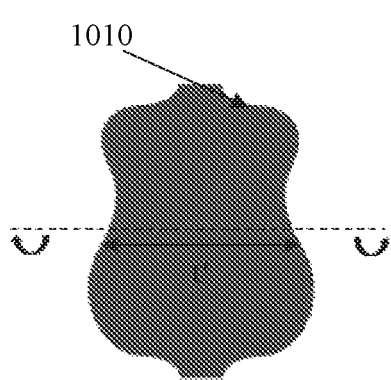
FIGS. 10A-C show views of a device according to some embodiments.
Figure 10B:
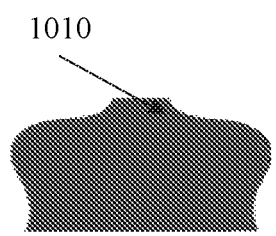
Figure 10C:
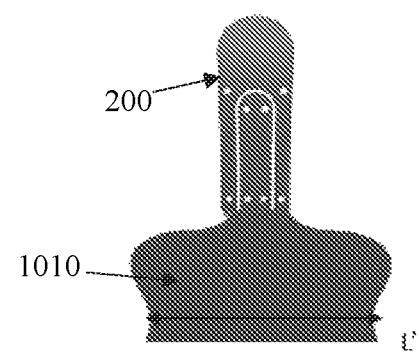

FIGS. 10A-10C show covering member 1010 having a length/that is longer than the length 1 of the member 910. FIG. 10A shows the flat material from which the covering member 1010 may be machined, FIG. 10B shows the machined covering member 1010 and the FIG. 10C shows the covering member 1010 disposed on the leaflet section 230 of the device body 200. Like covering member 910, the length 1 of the covering member 1010 is longer than the width of the leaflet section 230 so that the covering member 1010 covers and extends from the leaflet section 230.

In some embodiments, the first and second sections of the device in their default or first configuration can be machined to be close to each other, touch each other or cross each other. Using deforming forces, the first and second sections can also be pulled away from each other such that the gap between them can increase to the maximum degree possible (e.g., open configuration). The degree of such gap opening between the first and second sections may be dependent upon the operator, the forces with which they are deformed and separated, and/or the three-dimensional region/profile of the leaflet section. One or more of these different parameters can be optimized to achieve the maximal opening of the first (atrial) and second (ventricular) sections of the device under deforming forces.

For example, when disposed on the native leaflet, the disclosed device may be configured to alter the physical characteristics and properties of the leaflet onto which it is mounted, in a manner that it interacts and overlaps onto another leaflet of the same native valve in a better manner. The physical characteristics, properties, deformation, motion and stretch of the native leaflet at the site of the implantation of the device may be improved, but such changes at remote regions on the same leaflet may be expected as well. Changes in the native leaflet characteristics, properties, deformation, motion and stress of the leaflet on which the device is disposed, may enable improved interaction of this leaflet with the other leaflets of the same native valve in a manner that a desired clinical outcome is achieved.

By way of example, in some embodiments, the interaction between the native valve leaflet on which the device is disposed and other leaflets of the same native valve may be in a manner that the area of overlap between the leaflets may be altered. In other embodiments, the interaction between the native valve leaflet with the device and the other leaflets may be in a manner that a gap between the two leaflets may be eliminated in a certain part of the cardiac cycle. In some embodiments, the interaction between the native valve leaflet with the device and other leaflets may be in a manner that in some parts of the cardiac cycle, they may not be in physical contact and allow for flow of blood between the two leaflets.

In some embodiments, the native leaflet whose physical characteristics and properties that the device has altered, may interact with one or more of the other native leaflets of the same cardiac valve. The interaction may be such that some parts of the two leaflets may interact with one another via their native tissue, while other parts of the leaflet may interact with the surface of the device mounted on the other leaflet. The device can be used to achieve the desired clinical outcome whether the native tissue surface of the leaflets may be interacting or the native tissue surface of one leaflet may be interacting with the device. At the site where the device may interact with the native surface of another leaflet, it may do so in a manner that it deforms the leaflet it interacts with in a manner that it becomes parallel to the device surface and/or parallel to the tissue surface of the leaflet on which the device is mounted.

In some embodiments, for it may be possible that such parallelization of the leaflets may enable a larger surface of the tissue of one leaflet to overlap with the surface of another leaflet, or increase the surface of overlap between the tissue surface of one leaflet on to the device surface, or the surface of the device on one leaflet with the surface of the device on another leaflet. Such parallelization leading to an increase in the area of overlap between the native tissue surfaces of the two leaflets or the native tissue surface and the device on the other leaflet, or the surfaces of two devices on opposite leaflets, can reduce the leakage of blood through the valve in a certain phase of the cardiac cycle. Such parallelization and increased overlap between two surfaces in a certain phase of the cardiac cycle, can possibly reduce the overall stress distribution on the leaflets and the chordae tendineae of the mitral valve. Reduced stress distribution may increase the durability of the valve, by reducing the forces and stresses that the biological tissue may see over time and potentially reduce biological remodeling processes that may occur in response to stress, strain or forces.

In some embodiments of the device, increased thickness and/or increased leaflet length and/or increased leaflet height and/or extension of the leaflet shelf imparted by the device disposed onto the native valve leaflet, may enable covering a gap between the said leaflet and another leaflet of the same native valve during a specific phase of the cardiac cycle. In some embodiments, the device may cover the gap between the leaflets by passively covering the gap between the leaflets, while in some embodiments it may not only cover the gap between the leaflets, but also act a surface for the other leaflet to overlap onto. Such an overlap of the other leaflet onto the device in certain phases of the cardiac cycle, may alter the mobility of the leaflet in a manner that a desired clinical outcome may be achieved. In some other embodiments, overlap of the other leaflet onto the device in certain phases of the cardiac cycle, for example, the leaflet section 230, may eliminate the formation of a gap between the leaflets, which otherwise would form if the device were not deposed on a leaflet of the native valve.

Figure 11A:
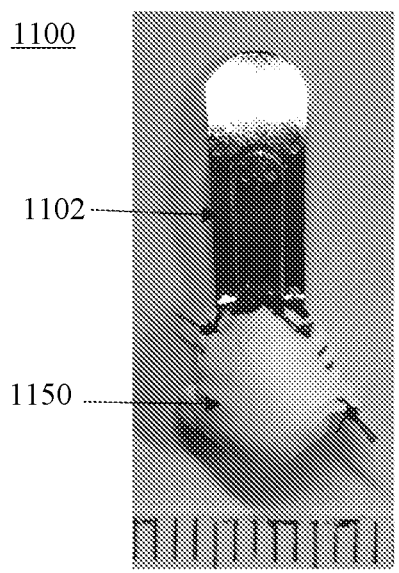
FIGS. 11A-C show views of a prototype according to some embodiments.
Figure 11B:
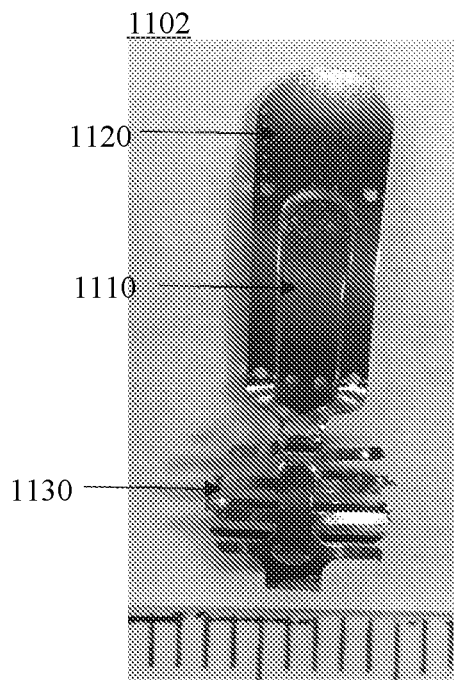
Figure 11C:
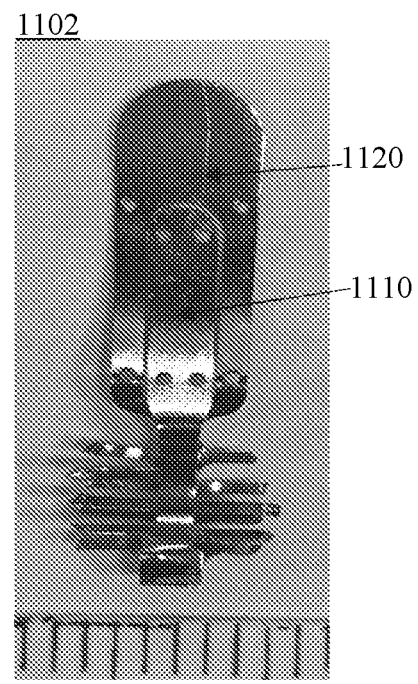

FIGS. 11A-C show views of an example of a prototype 1100. FIG. 11A shows a device body 1102 that includes a first section 1110, a second section 1120, and a leaflet section 1130, and a covering member 1150 that is disposed on the leaflet section 1130. FIGS. 11B and 11C show the device body 1102 without the covering member 1150. The device body 1102 is an example of a prototype of the device body 200 shown in FIGS. 2A-E. In this example, the prototype 1102 is machined from a flat sheet of Nitinol and the covering member 1150 is made of a composite layered stack of expanded polytetrafluoroethylene.

FIGS. 12A-D show an example 1200 of a delivery device or catheter 1210 configured to deliver the prototype device 1100, in an open configuration, according to embodiments.

FIG. 12A shows a front view of the catheter 1210 with the second (ventricular) second 1120 facing the user. As shown in this figure, the device 1100 may be removably fixed to the catheter 1210 by pulling the first section 1110 upwards to stabilize it, and the second section 1120 can be positioned in an open configuration by the suture 1240. FIG. 12B shows a side view of FIG. 12A. FIG. 12C shows a front view as 12A, but with the first section 1110 and the second section 1210 provided in the closed, default configuration. FIG. 12D shows a side view of FIG. 12C.

In some embodiments, the device 1100 may be delivered under image guidance to aid in locating the device at the native leaflet and enable its deposition on the native leaflet. The delivery device 1210 may include one or more coupling members disposed within a lumen and configured to be removably, fixedly dispose the device 1100 in an open configuration. In this example, the one or more coupling members may include a depression 1220 configured to receive the leaflet section 1130 and one or more openings 1222 configured to receive one or more sutures or wires 1240 for removably fixing the first section 1110 and/or the second section 1120 via the coupling members 1112. The first and second sections 1110 and 1120 may be removably disposed to the respective members of the delivery catheter to maintain the open configuration, for example, by using wire through the holes. The delivery catheter 1210 may include a sheath (not shown) to cover the device.

By way of example, the delivery catheter 1210 with the leaf enhancer device 1100 may be guided across the native mitral valve. After which, the delivery catheter may be unsheathed to expose the device and advance it into the left ventricle. After the delivery catheter is positioned at the leaflet, the first section 1110 may be gradually released causing it spring back to its pre-set or default configuration (e.g., closed/biased configuration) by controlling the tugging force on this portion of the device. Release of the first section 1110 may be performed after positioning the device 1100 such that the first section 1110 of the device 1100 can rest on the ventricular side of the desired native leaflet of the valve when released. After which, the other section (e.g., the second section) 1120 may be released resulting in the first and second sections 1110 and 1120 of the device 1100 being disposed on the native valve leaflet. The first and second sections 1110 and 1120 may compress the native leaflet in between them and thus provide good attachment of the device to the native leaflet. The delivery catheter may then be gradually retracted.

For example, increasing the tugging force on the first and second sections of the device would increase the gap between them (e.g., in the open configuration), while fully releasing the tugging force would enable springing back of these atrial and ventricular sections towards each other such that the gap is small, or they touch each other or cross over (e.g., closed configuration). When the tugging forces are released and the first and second sections spring back towards each other (e.g., closed configuration), they may compress the native leaflet in between them and thus provide good attachment of the device to the native leaflet.

Figure 13A:
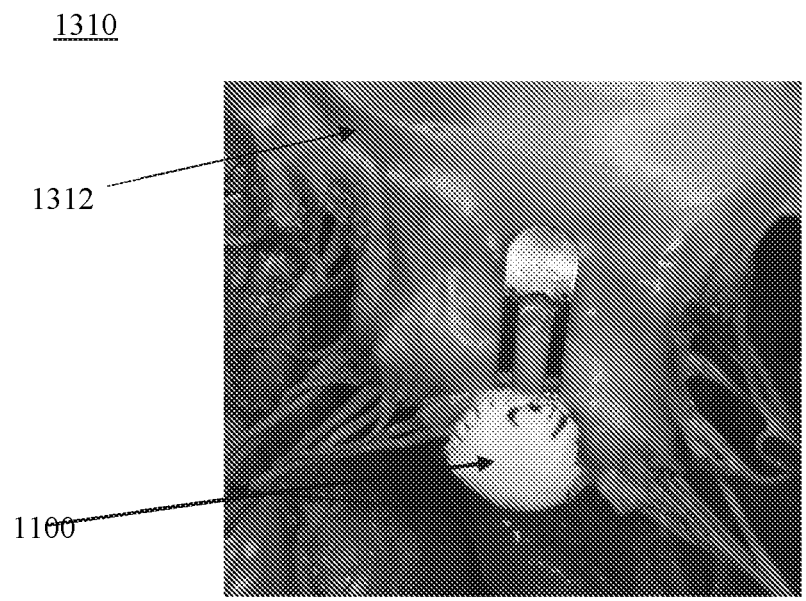
FIGS. 13A-B show the prototype shown in FIGS. 11A-C implanted on a native leaflet.
Figure 13B:
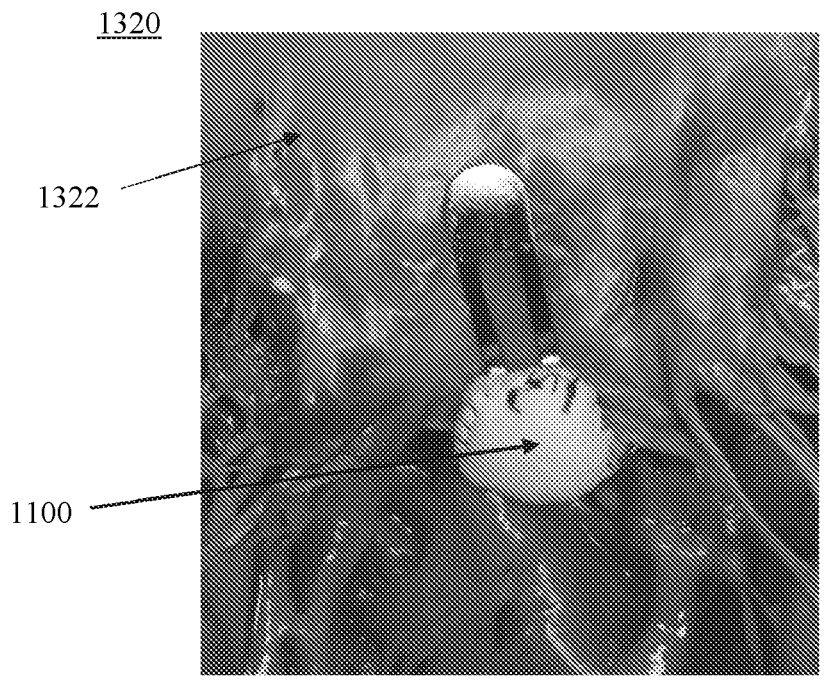

FIGS. 13A and B show examples 1310 and 1320 of the prototype device 1100 attached to or implanted on a native anterior leaflet 1312 and a posterior leaflet 1322, respectively. The device 1100 is disposed on the leaflet edge and thereby adds height, thickness and/or stiffness to this region. The device 1100 can be removed, adjusted, reattached or left remaining on the leaflet after the device is delivered and attached to a leaflet.

Figure 14A:
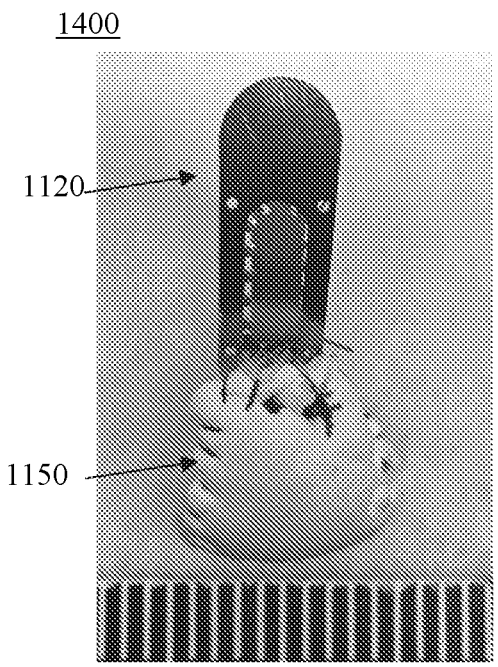
FIGS. 14A-D show views of a prototype according to some embodiments.

FIGS. 14A and B show different views of an example of a prototype 1400.

Figure 14B:
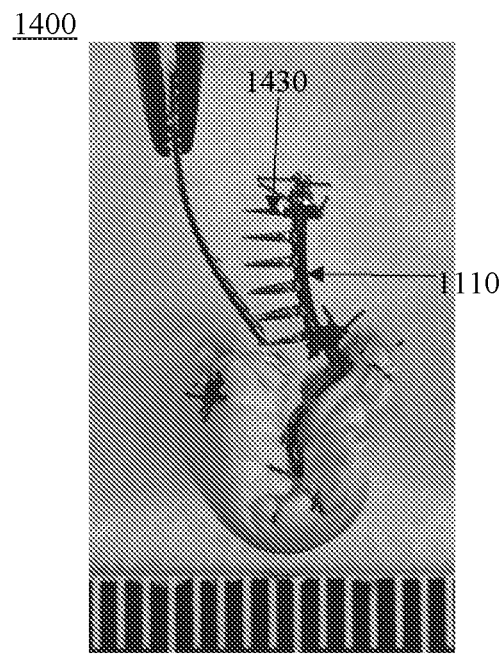
Figure 14C:
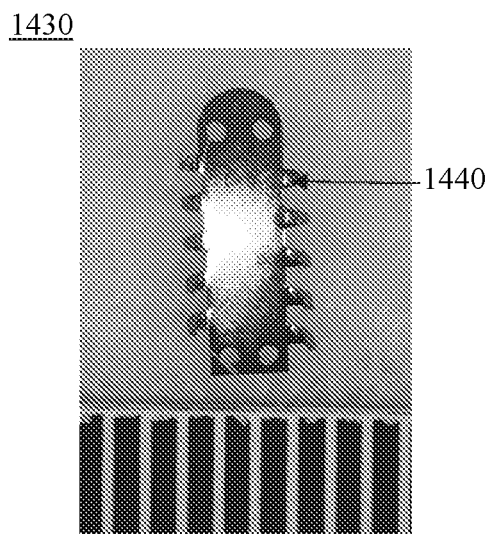
Figure 14D:
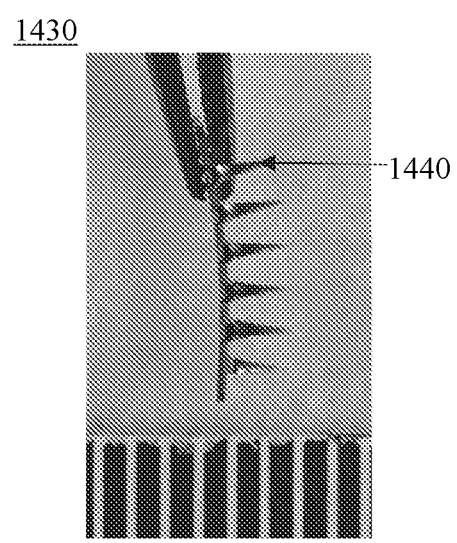

FIGS. 14A and 14B shows a device body 1120 on which a covering member 1150 is disposed on the leaflet section 1130 and an attachment member 1430 is disposed on the first section 1130. FIGS. 14C and 14D show views of the attachment member 1430. The attachment plate 1430 includes a plurality of tissue gripping members 1440 disposed on opposite side and protruding from the inner surface of the plate 1430. The attachment plate 1430 is an example of an attachment plate 300 shown in FIGS. 3A and 3B. In this example, the attachment plate 1430 is machined from a flat sheet of Nitinol. In this example, the attachment plate 1430 is attached to the first section 1130 using sutures via the coupling members. It will be understood that the attachment plate 1430 may be attached to the first section 1130 using other fasteners. In some embodiments, the tissue gripping members 1440 may integrated into the first section, for example, by machining the tissue gripping members 1440 from the single sheet that is used to machine the body 1120.

FIGS. 15A-C show views 1510, 1520, and 1530 of the prototype device 1400 attached to or implanted on a native leaflet 1512, respectively. For example, FIGS. 15B and C show the prototype device 1400 implanted on the anterior leaflet and the posterior side of the leaflet 1512, respectively. FIGS. 15A-C show the interaction between the tissue gripping members (e.g., teeth) 1440 and the rugged surface of the leaflet 1512, in a manner where the tissue gripping members 1440 sit into the crevices on the surface of the native leaflet 1512, thus can enable better attachment of the device 1400 to a leaflet 1512.

In some embodiments, the device 100 may be part of a kit. In some embodiments, the kit may include one or more of a device bodies, one or more accessories (e.g., attachment plate), one or more covering members, one or more fasteners, one or more delivery devices, one or more of other procedural materials/instruments, or any combination thereof. In some embodiments, a delivery device may be preloaded with the leaflet enhancer device. By way of example, the kit may include different accessories (e.g., attachment plate(s)) and/or covering members to be loaded onto the device body.

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed is:

1. A leaflet enhancer device, comprising:
   a leaflet section, the leaflet section defining a three-dimensional region and including a central member, the central member including a first portion, a second portion that opposes the first portion, and a base portion that is disposed between the first portion and the second portion;
   a first section extending from the first portion;
   a second section extending from the second portion, the second section larger than the first section and including an opening; and
   one or more engaging members extending at an angle from the central member,
   wherein the first section and the second section are at least partially coplanar and the first section is biased towards the second section such that the first section is disposed within the opening of the second section.

2. The device according to claim 1, wherein:
   the first portion and the second portion have a curved profile.

3. The device according to claim 2, wherein the first portion and the second portion protrude towards a direction relative to the planar profile of the first and second section to define a convex curved profile.

4. The device according to claim 1, wherein the one or more engaging members includes a first set of engaging members extending from the first portion and a second set of engaging members extending from the second portion.

5. The device according to claim 4, wherein the first set of engaging members includes less engaging members than the second set of engaging members.

6. The device according to claim 1, further comprising:
   a covering member, the covering member being disposed on and surrounding at least the leaflet section.

7. The device according to claim 1, wherein:
   the device is configured to move between (i) a default, closed position and (ii) an open position; and
   in the closed position, the first and second sections are configured to compress upon opposite surfaces of the native leaflet when the device is implanted.

8. The device according to claim 1, further comprising:
   one or more gripping members extending from a surface of the first section and/or a surface of the second section.

9. The device according to claim 8, further comprising:
   one or more plates configured to be attached to the first section and/or the second section, the one or more plates including the one or more gripping members.

10. The device according to claim 9, wherein the one or more plates includes a portion that extends within the leaflet section.

11. A leaflet enhancer device, comprising:
a leaflet section defining a three-dimensional region;
a first section extending from the leaflet section; and
a second section extending from the leaflet section, the second section including an opening;
wherein:
the second section is larger than the first section;
the device is configured to move between (i) a default, closed configuration and (ii) an open configuration;
the device is biased to the closed configuration;
in the closed configuration, the first section is biased towards the second section so that the first section and the second section are at least partially coplanar and the first section is disposed within the opening; and
in the closed configuration, the first section and the second section are configured to impose a compressive force on opposite surfaces of a native leaflet captured there between.

12. The device according to claim 11, wherein:
the leaflet section including a central member, the central member including a first portion, a second portion that opposes the first portion, and a base portion that is disposed between the first portion and the second portion;
the first section extends from the first portion; and
the second section extends from the second portion.

13. The device according to claim 11, further comprising:
one or more engaging members extending from the central member at an angle with respect to the first section and the second section.

14. The device according to claim 13,
wherein the one or more engaging members includes a first set of engaging members extending from the first portion and a second set of engaging members extending from the second portion.

15. The device according to claim 12, further comprising:
a covering member, the covering member being disposed on and surrounding at least the leaflet section.

16. The device according to claim 12, wherein:
the first portion protrudes towards the second portion; and
the leaflet section is configured to surround an edge of the native leaflet.

17. The device according to claim 11, further comprising:
one or more gripping members extending from a surface of the first section and/or a surface of the second section.

18. The device according to claim 17, further comprising:
one or more plates configured to be attached to the first section and/or the second section, the one or more plates including the one or more gripping members.

19. The device according to claim 18, wherein the one or more plates includes a portion that extends within the leaflet section.

20. The device according to claim 11, wherein the device is configured to be delivered using a delivery catheter, the delivery catheter being configured to deliver the device in the open configuration to the native leaflet and move the device to the closed configuration for attachment to the native leaflet.

* * * * *